(12) United States Patent
Wong et al.

(10) Patent No.: US 9,983,210 B2
(45) Date of Patent: May 29, 2018

(54) SALIVARY MRNA PROFILING, BIOMARKERS AND RELATED METHODS AND KITS OF PARTS

(71) Applicant: THE REGENTS OF THE UNIVERSITY OF CALIFORNIA, Oakland, CA (US)

(72) Inventors: David T. W. Wong, Beverly Hills, CA (US); Maie A. R. St. John, Los Angeles, CA (US); Yang Li, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 335 days.

(21) Appl. No.: 14/182,672

(22) Filed: Feb. 18, 2014

(65) Prior Publication Data
US 2014/0249236 A1     Sep. 4, 2014

Related U.S. Application Data

(63) Continuation of application No. 10/589,788, filed as application No. PCT/US2005/005263 on Feb. 17, 2005.

(60) Provisional application No. 60/546,507, filed on Feb. 20, 2004, provisional application No. 60/546,521, filed on Feb. 21, 2004.

(51) Int. Cl.
| G01N 33/53 | (2006.01) |
| G01N 33/574 | (2006.01) |
| G01N 33/50 | (2006.01) |
| G01N 33/68 | (2006.01) |

(52) U.S. Cl.
CPC ... *G01N 33/57488* (2013.01); *G01N 33/5017* (2013.01); *G01N 33/6893* (2013.01)

(58) Field of Classification Search
CPC ............................... G01N 33/50; G01N 33/53
See application file for complete search history.

(56) References Cited

U.S. PATENT DOCUMENTS

| 6,294,349 B1 * | 9/2001 | Streckfus | G01N 33/57415 435/7.1 |
| 6,511,805 B1 | 1/2003 | Gocke et al. | |
| 6,607,898 B1 | 8/2003 | Kopreski et al. | |
| 6,617,112 B2 | 9/2003 | Beals | |
| 6,759,217 B2 | 7/2004 | Kopreski | |
| 2002/0102553 A1 | 8/2002 | Coleman et al. | |
| 2003/0175770 A1 | 9/2003 | Gocke et al. | |

FOREIGN PATENT DOCUMENTS

| WO | 03/009806 A | 2/2003 |
| WO | 03/028531 A | 4/2003 |

OTHER PUBLICATIONS

Watanabe et al. (Role of Interleukin-8 secreted from human oral squamous cell carcinoma lines, 2002, Oral Oncology, vol. 38, pp. 670-679).*
Anon. 'GeneChip® Human Genome Arrays' Affymetrix Data Sheet [retrieved on Jun. 30, 2014]. Retrieved from Internet <http://media.affymetrix.com/support/technical/datasheets/human_datasheet.pdf> copyright 2003-2004.
Chen, Zhong et al., "Expression of Proinflammatory and Proangiogenic Cytokines in Patients with Head and Neck Cancer," 1999, Clinical Cancer Research, vol. 5, pp. 1369-1379.
Huang, Yu-Tzu et al., "Profile of Cytokine Expression in Nasopharyngeal Carcinomas: A Distinct Expression of Interleukin 1 in Tumor and $CD4^+$ T Cells," 1999, Cancer Research, vol. 59, pp. 1599-1605.
Gallo et al., "Interleukin-6 and acute-phase proteins in head and neck cancer," 1995, European Archives of Oto-Rhino-Laryncology, vol. 252, No. 3, pp. 159-162.
Jablonska et al., "TNF-alpha, IL-6 and their soluble receptor serum levels and secretion by neutrophils in cancer patients," 2001, Archivum Immunologiae ET Therapiae Experimentalis, vol. 49, No. 1, pp. 63-69.
Li et al., "Salivary Transcriptome Diagnostics for Oral Cancer Detection," Dec. 15, 2004, Clinical Cancer Research, vol. 10, No. 24, pp. 8442-8450.
Rhodus et al., "NF-kappaB dependent cytokine levels in saliva of patients with oral preneoplastic lesions and oral squamous cell carcinoma," 2005, Cancer Detection and Prevention, vol. 29, No. 1, pp. 42-45.
St John et al., "Interleukin 6 and interleukin 8 as potential biomarkers for oral cavity and oropharyngeal squamous cell carcinoma," Aug. 2004, Archives of Otolaryngology—Head and Neck Surgery, vol. 130, No. 8, pp. 929-935.
International Search Report dated Dec. 31, 2007, for PCT Application No. PCT/US05/25138 filed on Jul. 15, 2005, one page.

(Continued)

*Primary Examiner* — Prema Mertz
(74) *Attorney, Agent, or Firm* — Riverside Law LLP

(57) ABSTRACT

A method to detect a biomarker in saliva wherein the biomarker is an extracellular mRNA, comprises detecting the extracellular mRNA in the cell-free saliva; transcriptome analysis of saliva comprises detecting a transcriptome pattern in the cell-free saliva; a method to detect genetic alterations in an organ or in a gene in the organ by analyzing saliva, comprises detecting a transcriptome pattern and/or the mRNA profiling of the gene in cell-free saliva; a method to diagnose an oral or systemic pathology disease or disorder in a subject, comprises: detecting profile of a biomarker associated with the pathology disease or disorder, in particular mRNA and/or protein, in cell-free saliva and/or serum; kits comprising identifier for at least one biomarker for performing at least one of the methods; and use of salivary biomarker salivary and/or serum mRNAs as biomarkers for oral and/or systemic pathology, disease or disorder.

6 Claims, 11 Drawing Sheets

(56) References Cited

OTHER PUBLICATIONS

Shugars, D.C. et al., "Oral and systemic factors associated with increased levels of human immunodeficiency virus type 1 RNA in saliva," Apr. 2000, *Oral Surgery Oral Medicine Oral Pathology*, vol. 89, No. 4, pp. 2-10.
Sun et al., "Gene expression profiling on lung cancer outcome prediction: present clinical value and future premise," 2006, *Cancer Epidemiology, Biomarkers and Prevention*, vol. 15, pp. 2063-2068.
Ziober et al., "Lab-on-a-chip for oral cancer screening and diagnosis," 2008, *Head and Neck*, vol. 30, pp. 111-121.
Westra et al., "Toward early oral cancer detection using gene expression profiling of saliva: a thoroughfare or a dead end?" 2004, *Clinical Cancer Research*, vol. 10, pp. 8130-8131.
Squire et al., "Molecular cytogenetic analysis of head and neck squamous cell carcinoma: by comparative genetic hybridization, spectral karyotyping, and expression array analysis," 2002, *Head and Neck*, vol. 24, pp. 874-887.
Juusola, J. et al., "mRNA profiling: a prototype method to supplant conventional methods for body fluid identification," 2003, *Forensic Science International*, vol. 135, pp. 85-96.
"Affymetrix GeneChip Human Genome U133 Array Set HG-U133A," GEO (2002).
El-Naggar et al., "Genetic heterogeneity in saliva from patients with oral squamous carcinomas: implications in molecular diagnosis and screening," 2001, *Journal of Molecular Diagnostics*, vol. 3, Nov. 4, pp. 164-170.
Ibrahim et al., "Gene expression profile in oral squamous cell carcinomas and matching normal oral mucosal tissues from black Africans and white Caucasians: the case of the Sudan vs. Norway," 2003, *Oral Oncology*, vol. 39, No. 1, pp. 37-48.

\* cited by examiner

SALIVARY MRNA PROFILING, BIOMARKERS AND RELATED METHODS AND KITS OF PARTS

CROSS-REFERENCE TO RELATED APPLICATIONS

This Application is a continuation of U.S. patent application Ser. No. 10/589,788, filed May 25, 2007, which is the U.S. National Phase Application filed under 35 U.S.C. § 371 claiming benefit to International Patent Application No. PCT/US2005/005263 filed on Feb. 17, 2005, which is entitled to priority under 35 U.S.C. § 119(e) to U.S. Provisional Patent Application No. 60/546,507 filed Feb. 20, 2004 and U.S. Provisional Patent Application No. 60/546,521 filed Feb. 21, 2004, all of which applications are incorporated herein by reference in their entireties.

This invention was made with Government support under DE015018 awarded by the National Institutes of Health. The Government has certain rights in the invention.

FIELD OF THE DISCLOSURE

The present disclosure relates to profiling of biomarkers and to method and kits using said biomarkers. In particular, the present disclosure related to biomarkers for detection of cancer and in particular of Oral Cavity and Oropharyngeal squamous Cell Carcinoma (OSCC).

BACKGROUND OF THE DISCLOSURE

Biomarkers are molecular indicators of a specific biological property, a biochemical feature or facet that can be used to measure the progress of disease or the effects of treatment.

Proteins and nucleic acids are exemplary biomarkers. In particular, it has been widely accepted that genomic messengers detected extracellularly can serve as biomarkers for diseases [6]. In particular, nucleic acids have been identified in most bodily fluids including blood, urine and cerebrospinal fluid, and have been successfully adopted for using as diagnostic biomarkers for diseases [28, 42, 49].

Saliva is not a passive "ultrafiltrate" of serum [41], but contains a distinctive composition of enzymes, hormones, antibodies, and other molecules. In the past 10 years, the use of saliva as a diagnostic fluid has been successfully applied in diagnostics and predicting populations at risk for a variety of conditions [47].

Specific and informative biomarkers in saliva are desirable to serve for diagnosing disease and monitoring human health [30, 47, 6]. For example biomarkers have been identified in saliva for monitoring caries, periodontitis, oral cancer, salivary gland diseases, and systemic disorders, e.g., hepatitis and HIV [35]. Also previous studies show that human DNA biomarkers can be identified in saliva and used for oral cancer detection [30, 36]. RNA is more labile than DNA and is presumed to be highly susceptible to degradation by RNases. Furthermore, RNase activity, is reported to be elevated in saliva, which constitutes an inexpensive, non-invasive and accessible bodily fluid suitable to act as an ideal diagnostic medium. In particular, RNAase activity is reported to be elevated in saliva of cancer patients [83]. It has, thus, been commonly presumed that human mRNA could not survive extracellularly in saliva. OSCC is the sixth most common cancer in the world, and affects 50,000 Americans annually. Worldwide, cancers of the oral cavity and oropharynx represent a great public health problem. OSCC accounts for nearly 50% of all newly diagnosed cancers in India and is a leading cause of death in France [1].

Despite improvements in locoregional control, morbidity and mortality rates have improved little in the past 30 years [2]. Therefore, early detection or prevention of this disease is likely to be most effective. Detecting OSCC at an early stage is believed to be the most effective means to reduce death and disfigurement from this disease. The absence of definite early warning signs for most head and neck cancers suggests that sensitive and specific biomarkers are likely to be important in screening high risk patients.

SUMMARY OF THE DISCLOSURE

According to a first aspect, a method to detect a biomarker in a bodily fluid including a cell phase and a fluid phase, wherein the biomarker is an extracellular mRNA and bodily fluid is saliva, preferably unstimulated saliva, is disclosed. The method comprises: providing a cell-free fluid phase portion of the bodily fluid; and detecting the extracellular mRNA in the cell-free fluid phase portion of the bodily fluid.

In particular, detecting the extracellular mRNA can comprise: isolating the extracellular mRNA from the cell-free fluid phase portion of the bodily fluid, and amplifying the extracellular mRNA.

According to a second aspect, transcriptome analysis of a bodily fluid, including a cell phase and a fluid phase, wherein the bodily fluid is saliva, is disclosed. The method comprises: providing a cell-free fluid phase portion of the bodily fluid; and detecting a transcriptome pattern in the cell-free fluid phase portion of the bodily fluid. The bodily fluid is preferably unstimulated saliva.

In particular, detecting transcriptome pattern in the saliva supernatant is preferably performed by microarray assay, most preferably by high-density oligonucleotide microarray assay. Detecting transcriptome pattern in the saliva supernatant can also performed by quantitative PCR analysis or RT-PCR analysis.

According to a third aspect, a method to detect genetic alterations in an organ by analyzing a bodily fluid draining from the organ and including a cell phase and a fluid phase, is disclosed. The bodily fluid is in particular saliva, preferably unstimulated saliva and method comprises: providing cell-free fluid phase portion of the bodily fluid; detecting a transcriptome pattern in the cell-free fluid phase portion of the bodily fluid; and comparing the transcriptome pattern with a predetermined pattern, the predetermined pattern being indicative of a common transcriptome pattern of normal cell-free fluid phase portion of the bodily fluid.

According to a fourth aspect, a method to detect genetic alteration of a gene in an organ by analyzing a bodily fluid draining from the organ and including a cell phase and a fluid phase, is disclosed. The bodily fluid is in particular saliva and the method comprises: providing a cell-free fluid phase portion of the bodily fluid; detecting an mRNA profile of the gene in the cell-free fluid phase portion of the bodily fluid; and comparing the mRNA profile of the gene with a predetermined mRNA profile of the gene, the predetermined mRNA profile of the gene being indicative of the mRNA profile of the gene in normal cell-free fluid phase portion of the bodily fluid.

According to a fifth aspect, a method to diagnose an oral or systemic pathology disease or disorder in a subject, is disclosed. The method comprises: providing a cell-free fluid phase portion of the saliva or the subject, detecting in the provided cell-free saliva fluid phase portion an mRNA profile of a gene associated with the pathology, disease or disorder; and comparing the RNA profile of the gene with a predetermined mRNA profile of the gene, the predetermined mRNA profile of the gene being indicative of the presence of the pathology, disease, or disorder in the subject.

In a first embodiment the pathology, disease or disorder is a cancer of the oral cavity and/or of oropharynx, the bodily fluid is saliva and the gene is selected from the group consisting of the gene coding for IL8 (Interleukin 8), IL1B (Interleukin 1, beta), DUSP1 (Dual specificity phosphatase 1), H3F3A (H3 histone, family 3A), OAZ1 (Ornithine decarboxylase antizyme 1), S100P (S100 calcium binding protein P) and SAT (Spermidine/spermine N1-acetyltransferase).

In a second embodiment the pathology, disease or disorder is a cancer of the oral cavity and/or of oropharynx, the bodily fluid is blood serum and the gene is selected IL6 (interleukin 6), H3F3A, TPT1(Tumor protein translationally controlled 1), FTH1 (Ferritin heavy polypeptide 1), NCOA4 (Nuclear receptor coactivator 4) and ARCR (Ras homolog gene family, member A).

Diseases that can be diagnosed include oropharyngeal squamous cell carcinoma and possibly other systemic diseases.

According to a sixth aspect, a method to diagnose an oral or systemic pathology, disease or disorder in a subject is disclosed. The method comprises: providing a cell-free fluid phase portion of the saliva of the subject; detecting in the provided cell-free fluid phase portion a transcriptome pattern associated with the pathology, disease or disorder; and comparing the transcriptome pattern with a predetermined pattern, recognition in the transcriptome pattern of characteristics of the predetermined pattern being diagnostic for the pathology, disease or disorder in the subject.

In an embodiment, the pathology, disease or disorder is a cancer of the oral cavity and/or of oropharynx, and transcriptome include transcript is selected from the group consisting of transcripts for IL8, IL1B, DUSP1, H3F3A, OAZ1, S1 OOP, SAT from saliva.

According to a seventh aspect, a method to diagnose an oral or systemic pathology, disease or disorder in a subject is disclosed, the method comprising: providing serum of the subject; detecting in the provided serum a transcriptome pattern associated with the pathology, disease or disorder; and comparing the transcriptome pattern with a predetermined pattern, recognition in the transcriptome pattern of characteristics of the predetermined pattern being diagnostic for the pathology, disease or disorder in the subject.

In an embodiment, the pathology, disease or disorder is a cancer of the oral cavity and/or of oropharynx, and transcriptome include transcript is selected from the group consisting of transcripts for IL6, H3F3A, TPT1, FTH1, NCOA4 and ARCR from serum.

Diseases that can be diagnosed include oropharyngeal squamous cell carcinoma possibly other systemic diseases.

According to a eight aspect, a method for diagnosing a cancer, in a subject is disclosed. The method comprises: providing a bodily fluid of the subject; detecting in the bodily fluid a profile of a biomarker, comparing the profile of the biomarker with a predetermined profile of the biomarker, recognition in the profile of the biomarker of characteristics of the predetermined profile of the biomarker being diagnostic for the cancer.

Pathologies, diseases or disorders that can be diagnosed include oropharyngeal squamous cell carcinoma and possibly other systemic diseases. Biomarkers include IL8, IL1B, DUSP1, H3F3A, OAZ1, S100P, SAT, IL6, H3F3A, TPT1, FTH 1, NCOA4 and ARCR.

In a first embodiment, the pathology, disease or disorder is oropharyngeal squamous cell carcinoma, the biomarker is selected from the group consisting of IL8 IL1B, DUSP1, H3F3A, OAZ1, S100P, SAT, the bodily fluid is saliva and detecting a profile or a biomarker is performed by detecting the mRNA profile of the biomarker.

In a second embodiment, the pathology, disease or disorder is oropharyngeal squamous cell carcinoma, the biomarker is selected from the group consisting of IL6, H3F3A, TPT1, FTH1, NCOA4 and ARCR the bodily fluid is serum and detecting a profile of a biomarker is performed by detecting the mRNA profile of the biomarker.

In a third embodiment, the pathology, disease or disorder is oropharyngeal squamous cell carcinoma, the biomarker is IL6, the bodily fluid is blood serum and detecting a profile of a biomarker is performed by detecting the protein profile of the biomarker According to an eighth aspect, a kit for the diagnosis of an oral and/or systemic pathology, disease or disorder is disclosed, the kit comprising: an identifier of at least one biomarker in a bodily fluid, the biomarker selected from the group consisting of IL8, IL1B, DUSP1, H3F3A, OAZ1, S100P, SAT, IL6, H3F3A, TPT1, FTH1, NCOA4 and ARCR; and a detector for the identifier.

Pathologies, diseases or disorders that can be diagnosed include oropharyngeal squamous cell carcinoma, and possibly the other systemic diseases.

The identifier and the detector are to be used in detecting the bodily fluid profile of the biomarker according to the methods herein disclosed. In particular, the identifier is associated to the biomarker in the bodily fluid, and the detector is used to detect the identifier, the identifier and the detector thereby enables the detection of the bodily fluid profile of the biomarker.

According to a ninth aspect, a method to diagnose an oral and/or systemic pathology disease or disorder, is disclosed. The method comprising: using salivary and/or serum mRNAs as biomarkers for oral and/or systemic pathology, disease or disorder.

In a preferred embodiment the MRNA codifies for at least one of the biomarker selected from the group consisting of IL8, IL1B, DUSP1, H3F3A, OAZ1, S100P, SAT, IL6, H3F3A, TPT1, FTH1, NCOA4 and ARCR.

Diseases that can be diagnosed include oropharyngeal squamous cell carcinoma, and possibly other systemic diseases.

According to a tenth aspect, a method to diagnose an oral and/or system pathology, is disclosed. The method comprising: using salivary or serum proteins as biomarkers for oral and/or systemic pathology, disease or disorder, in particular IL6 protein in serum and IL8 protein in saliva.

The methods and kits of the disclosure will be exemplified with the aid of the enclosed figures.

DETAILED DESCRIPTION OF THE PREFERRED EMBODIMENTS

Figure 1:
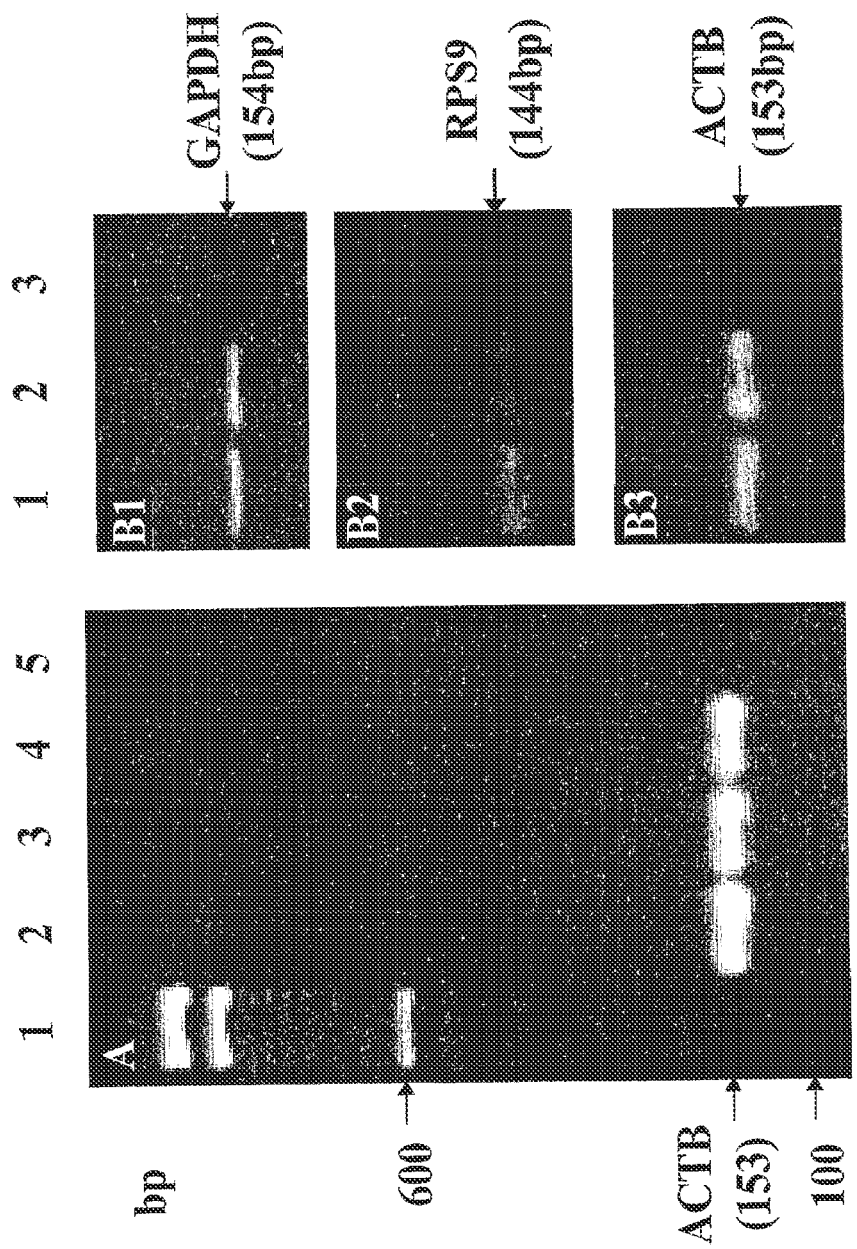
FIG. 1A shows results of a RT-PCR typing for ACTB performed on RNA isolated from cell-free saliva supernatant from human beings after storage for 1 month (lane 2), 3 months (lane 3) and 6 months (lane 4), with a 100 bp ladder molecular weight marker (lane 1) and a negative control (omitting templates) (lane 5). A molecular size marker is indicated on the left side of the Figure by arrows.
FIG. 1B shows results of a RT-PCR performed on RNA isolated from cell-free saliva supernatant from human beings (lane 1) and typing GAPDH (B1), RPS9 (B2) and ACTB (B3), with positive control (human total RNA, BD Biosciences Clontech, Palo Alto, Calif., USA) (lane 2) and negative controls (omitting templates) (lane 3). A molecular size marker is indicated on the left side of the Figure by arrows.

A method to detect an extracellular mRNA in a bodily fluid, is disclosed wherein the bodily fluid is saliva and the extracellular mRNA is detected in a cell-free fluid phase portion of saliva. Presence of RNAs in the cell-free fluid phase portion of saliva was confirmed by the procedures extensively described in the Examples, the quality of the detected mRNA meeting the demand for techniques such as PCR, qPCR, and microarray assays.

In the method, detecting extracellular mRNAs herein also informative mRNAs, is performed in a bodily fluid, saliva, that meets the demands of an inexpensive, non-invasive and accessible bodily fluid to act as an ideal medium for investigative analysis.

Detecting informative mRNAs is in particular performed in a portion of saliva (cell-free fluid phase) wherein presence of microorganisms and the extraneous substances such as food debris is minimized, which allows analyzing the molecules in simple and accurate fashion. Preferably, the cell-free fluid phase portion of derived from unstimulated saliva.

In the method, the saliva can be collected according to procedures known in the art and then processed to derive the cell-free fluid phase thereof, for example by centrifugation of the collected saliva, which results in a pelleted saliva cell phase and a cell-free saliva fluid phase supernatant. (see procedures extensively described in Examples 1, 5 and 13)

According to the present disclosure, the conditions for separating the cell-phase and the fluid phase of saliva are optimized to avoid mechanical rupture of cellular elements which would contribute to the RNA detected in the fluid cell-free phase.

In embodiments wherein the separation is performed by centrifugation, optimization can be performed by testing housekeeping genes on samples centrifuged at various speed and on whole saliva samples, using DNA as a marker of cell lysis and spillage, to derive the optimized centrifugation speed. (See procedure described in Example 5).

Detection of the extracellular mRNA in the cell-free saliva fluid phase portion (salivary mRNA) can then be performed by techniques known in the art allowing mRNA qualitative and/or a quantitative analysis, such as RT-PCR, Q-PCR and Microarray. The detection can in particular be performed according to procedures that can include isolation and an amplification of the salivary mRNA and that are exemplified in the Examples.

Detection of the salivary mRNA in the method can be performed for the purpose of profiling the salivary mRNA.

In a first series of embodiments, the expression of predetermined genes, can be profiled in a cell-free fluid phase portion of saliva. In those embodiments, detection of the mRNA profile can be performed by RT-PCR or any techniques allowing identification of a predetermined target mRNA. Quantitative analysis can then be performed with techniques such as Quantitative PCR (Q-PCR) to confirm the presence of mRNA identified by the RT-PCR. A reference database can then be generated based on the mRNA profiles so obtained. Exemplary procedures to perform such qualitative and quantitative analyses of salivary mRNA are described in details in Examples 1, 4 and 9.

In a second series of embodiments, a transcriptome analysis of saliva can be performed by detecting a transcriptome pattern in the cell-free fluid phase portion of saliva. Detection of the transcriptome pattern can be performed by isolating and linearly amplifying salivary mRNA, which can then be profiled with techniques such as high-density oligonucleotide microarrays. Quantitative analysis can then be performed with techniques such as Q-PCR to confirm the presence of mRNA in the pattern identified by the microarray. A reference database can then be generated based on the mRNA profiles so obtained. Exemplary procedures to perform such qualitative and quantitative analyses of salivary mRNA are described in details in Examples 2-3, 9-10 and 14-15.

Profiling salivary RNA can be performed to detect and/or monitor human health and disease or to investigate biological questions, such as for example, the origin, release and clearance of mRNA in saliva. The salivary mRNA provides actual or potential biomarkers to identify populations and patients at high risk for oral and systemic pathologies, diseases or disorders.

Alterations of the salivary mRNA profiles and transcriptome patterns characterizing the cell-free fluid phase portion of saliva or normal subjects can be indicative of pathologies, diseases or disorders of various origin. Examples of those pathologies, diseases or disorders are provided by the inflammatory conditions of the oral cavity, OSCC or other conditions such as diabetes, breast cancer and HIV.

Also comparison between the mRNA profiles and transcriptome patterns of subject affected with a determined pathology, disease or disorder, can result in the identification of informative biomarkers for the determined pathology disease or disorder. In particular, salivary mRNA can be used as diagnostic biomarkers for oral and systemic pathologies, diseases or disorders that may be manifested in the oral cavity.

In particular, salivary mRNA can be used as diagnostic biomarkers for cancer that may be manifested and/or affect the oral cavity. Saliva-based mRNA assays have the needed specificity and sensitivity for reliable diagnostics.

In case of various forms of cancer, alterations of the normal salivary mRNA and transcriptome patterns can also reflect the genetic alterations in one or more portions of the oral cavity which are associated with presence of the tumor. For oral cancer patients, the detected cancer-associated RNA signature is likely to originate from the matched tumor and/or a systemic response (local or distal) that further reflects itself in the whole saliva corning from each of the three major sources (salivary glands, gingival crevicular fluid, and oral mucosal cells). It is conceivable that disease-associated RNA can find its way into the oral cavity via the salivary gland or circulation through the gingival crevicular fluid. A good example is the elevated presence of HER-2 proteins in saliva of breast cancer patients [87].

A common transcriptome of normal cell-free saliva, including approximately 185 different human mRNAs, also defined as Normal Salivary Core Transcriptome (NSCT) was identified in outcome of a transcriptome analysis performed on cell-free fluid phase of saliva from normal subject (see Example 2, Table 2).

Since the NSCT was identified using the probe sets on HG U133A microarray representing only ~19,000 human genes, and the human genome composed of more than 30,000 genes [48], it is expected that more human mRNAs will be identified in saliva by other methodologies and additional salivary patterns are identifiable by the method herein disclosed.

The NSCT and/or other salivary transcriptome patterns in cell-free saliva from normal populations can serve in a Salivary Transcriptome Diagnostics (SlvTD), for potential applications in disease diagnostics as well as normal health surveillance.

Accordingly, in a first embodiment of the SlvTD, a method to diagnose an oral or systemic pathology disease or disorder in a subject, is disclosed. The method comprises: providing a cell-free fluid phase portion of the saliva of the subject; detecting in the provided cell-free saliva fluid phase portion an mRNA profile of a gene associated with the disease; and comparing the RNA profile of the gene with a predetermined mRNA profile of the gene, the predetermined mRNA profile of the gene being indicative of the presence of the disease in the subject.

In a second embodiment of the SlvTD, a method to diagnose an oral or systemic pathology disease or disorder in a subject, is disclosed. The method comprises: providing cell-free saliva supernatant of the subject; detecting in the cell-free saliva supernatant a transcriptome pattern associated with the pathology disease or disorder; and comparing the transcriptome pattern with a predetermined pattern, recognition in the transcriptome pattern of characteristics of the predetermined pattern being diagnostic for the pathology disease or disorder in the subject.

In a third embodiment of the SlvTD, a method to identify a biomarker associated with a predetermined pathology disease or disorder is disclosed. The method comprises: detecting a first mRNA profiling of a predetermined gene in cell-free fluid phase portion of saliva of a subject affected by the pathology disease or disorder; detecting a second mRNA profiling of the predetermined gene in cell-free fluid phase portion of saliva of a normal subject; comparing the first mRNA profiling with the second mRNA profiling, recognition of differences between the first mRNA profiling and the second mRNA profiling, the differences validated by statistical analysis, being indicative of the identification of the predetermined gene as a biomarker for the predetermined pathology disease or disorder.

In particular the difference between the RNA profiling from one disease category to one healthy category is analyzed by microarray statistical methodologies. The algorithms used include MAS 5.0, DNA-Chip analyzer 1.3 and RMA 3.0. Preferably, the analysis is performed by a combination of these methods to provide more powerful and accurate markers to test. The markers identified by microarray will then be tested by conventional techniques such as Q-PCR.

In a fourth embodiment of the SlvTD a diagnostic method can be performed, wherein the cell-free saliva is contacted with an identifier for the presence or expression of the biomarker, and the presence of the identifier associated to presence or expression of the biomarker is detected, preferably by means of a detector.

The SlvTD allow detection of diseases such as tumors at a stage early enough that treatment is likely to be successful, with screening tools exhibiting the combined features of high sensitivity and high specificity. Moreover, the screening tool are sufficiently noninvasive and inexpensive to allow widespread applicability.

The results of the above methods of the SlvTD can be integrated with a corresponding analysis performed at an mRNA and/or protein level and/or in other bodily fluid, such as blood serum.

Biomarkers, such as protein or transcriptome patterns detected in serum can also serve in a Serum Transcriptome Diagnostics (SrmTD), for potential applications in disease diagnostics as well as normal health surveillance. Embodiments of the SrmTD include methods corresponding to the ones reported above for the SlvTD, wherein the bodily fluid analyzed is serum instead of cell-free saliva.

In particular, the results obtained following the SlvTD can be combined with results obtained with the SrmTD, in a combined Salivary and Serum Transicriptome approach (SSTD)

According to the SSTD a diagnostic method can be performed, wherein the bodily fluid, serum and/or saliva is contacted with an identifier for the presence or expression of the biomarker, wherein the biomarker can be a protein or an mRNA and the presence of the identifier associated to presence or expression of the biomarker is detected, preferably by means of a detector.

Examples of the SlvTD, SrmTD and SSTD are herein provided with reference to the OSCC. The person skilled in the art can derive the appropriate modifications of the STD herein exemplified for diseases different than OSCC upon reading of the present disclosure.

Profiling of two specific cytokines, IL6 and IL8, was measured in the cell-free fluid phase portion of saliva and serum of patients with OSCC according to procedures extensively disclosed in Examples 4-8. IL8 was detected at higher concentrations in the saliva of patients with OSCC (P<0.01) and IL6 was detected at higher concentrations in the serum of patients with OSCC (P<0.01). These results were confirmed at both the mRNA and the protein levels, and the results were concordant. The concentration of IL8 in saliva and IL6 in serum did not appear to be associated with gender, age, or alcohol or tobacco use (P>0.75). The data were subjected to statistical analysis, in particular to ROC analysis, and were able to determine the threshold value, sensitivity, and specificity of each biomarker for detecting OSCC (see Example 8, Table 3). Furthermore, the inventors were able to measure mRNA in salivary specimens.

A transcriptome analysis of unstimulated saliva collected from patients with OSCC and normal subjects was performed as disclosed in Examples 9-12 and in Examples 13-16.

RNA isolation was performed from the saliva supernatant, followed by two-round linear amplification with T7 RNA polymerase. Human Genome U133A microarrays were applied for profiling human salivary transcriptome. The different gene expression patterns were analyzed by combining a t test comparison and a fold-change analysis on 10 matched cancer patients and controls. Quantitative polymerase chain reaction (qPCR) was used to validate the selected genes that showed significant difference (P<0.01) by microarray. The predictive power of these salivary mRNA biomarkers was analyzed by receiver operating characteristic curve and classification models.

The results of a first set of microarray analysis showed that there are 1,679 genes exhibited significantly different expression level in saliva between cancer patients and controls (P<0.05). Seven cancer-related mRNA biomarkers that exhibited at least a 3.5-fold elevation in OSCC saliva (P<0.01) were consistently validated by qPCR on saliva samples from OSCC patients (n=32) and controls (n=32). These salivary RNA biomarkers are transcripts of IL8, IL1B, DUSP1, H3F3A, OAZ1, S 100P, and SAT. The combinations of these biomarkers yielded sensitivity (91%) and specificity (91%) in distinguishing OSCC from the controls. (see Examples 13-16)

The results of a second set of microarray analysis showed five of ten up-regulated genes selected based on their reported cancer-association, showed significantly elevated transcripts in serum of OSCC patient. These RNA biomarkers are transcripts of H3F3A, TPT1, FTH1, NCOA4 and ARCR. The results validated by qPCR confirmed that transcripts of these five genes were significantly elevated in the serum of OSCC patient (Wilcoxon Signed Rank test, P<0.05). (See Examples 9 to 12)

Using the described collection and processing protocols, the presence of ACTB, B2W, GAPDH and RPS9 mRNAs (controls mRNA) were confirmed in all serum (patients and controls) by RT-PCR.

Accordingly, a method for diagnosing a cancer, in particular OSCC in a subject, is disclosed. The method comprises: providing a bodily fluids of the subject; detecting in the bodily fluid a profile of a bit) marker, the biomarker selected from the group consisting of IL8 IL1B, DUSP1, H3F3A, OAZ1, S100P, SAT, IL6, H3F3A, TPT1, FTH1, NCOA4 and ARCR, comparing the profile of the biomarker with a predetermined profile of the biomarker, recognition in the profile of the biomarker of characteristics of the predetermined profile of the biomarker being diagnostic for the cancer.

Also method to diagnose oral and/or systemic pathology, disease or disorder, in particular OSCC, is disclosed. The method comprises using salivary mRNAs as biomarkers for oral and/or systemic diseases, in particular salivary mRNAs of selected from the group consisting of IL8 IL1B, DUSP1, H3F3A, OAZ1, S100P and SAT.

Additionally a method to diagnose oral and/or systemic pathology, disease or disorder, in particular OSCC, is disclosed. The method comprises: using serum MRNAs and/or protein as biomarkers for oral and/or systemic diseases, in particular serum mRNAs of selected from the group consisting of IL6, H3F3A, TPT1, FTH1, NCOA4 and ARCR, and serum IL6 protein.

Given the multifactorial nature of oncogenesis and the heterogeneity in oncogenic pathways use of combinations of salivary and/or serum biomarkers, ensuring higher specificity and sensitivity, to detect the disease, is preferred. Multiple statistical strategies reported and risk models described in the examples can be used to identify combinations of biomarkers that can identify OSCC patients samples and to facilitate assigning the appropriate serum transcriptome-based diagnosis for patients' specific cancer risk.

Monitoring of profile of salivary mRNA in cell-free fluid phase portion of saliva and/or in other bodily fluid such as blood serum, can be used in the postoperative management of OSCC patients. It could potentially be used for monitoring the efficacy of treatment, or disease recurrence after therapy has concluded. Salivary mRNAs and in particular IL8 may also serve as prognostic indicators to direct the treatment of patients with oral cavity cancer. In perspective, high-risk patients can be directed to more aggressive or adjuvant treatment regimens.

The use of these biomarkers may also improve the staging of the tumor. With traditional techniques, the presence of microscopic distant disease is often under recognized. In recent years, there has been a shift from locoregional failure to distant failure for patients treated for presumed locoregional disease.[18] This in part is a reflection of subclinical distant disease present prior to the initiation of therapy. Testing for the presence of biomarkers may allow the detection of small amounts of tumor cells in a background of normal tissue. Salivary mRNAs as biomarkers specific for head and neck tumors or a panel of such biomarkers may allow the detection of distant microscopic disease. For oral cancer, one of the most important applications of the STD approach in this respect is to detect the cancer conversion of oral premalignant lesions.

Profiling of salivary mRNAs can also be used to investigate the role of genes in the development of cancer, in particular whether the aberrant expressions of these genes functionally contribute to the development of human OSCC. The biological significance of differential expression of these genes in head and neck/oral cancer should be determined. Identification of cancer-associated genes that are consistently changed in cancer patients will provide us not only with diagnostic markers but also with insights about molecular profiles involved in head and neck cancer development. Understanding the profile of molecular changes in any particular cancer will be extremely useful because it will become possible to correlate the resulting phenotype of that cancer with molecular events.

Kits of parts associated with the methods herein disclosed are also disclosed. In an exemplary embodiment, a kit comprises: a identifier of a biomarker in a bodily fluid, such as a salivary mRNA or protein, and serum mRNA or protein, the biomarker selected from the group consisting of IL8 IL1B, DUSP1, H3F3A, OAZ1, S100P, SAT, IL6, H3F3A, TPT1, FTH1, NCOA4 and ARCR; and a detector for the identifier, the identifier and the detector to be used in detecting the bodily fluid profile of the biomarker of one the methods herein disclosed, wherein the identifier is associated to the biomarker in the bodily fluid, and the detector is used to detect the identifier, the identifier and the detector thereby enabling the detection of the bodily fluid profile of the biomarker.

The bodily fluid can be saliva, with the detection performed in the cell-free fluid phase portion thereof, or another bodily fluid such as blood serum.

The identifier and the detector able to detect the identifier, are identifiable by a person skilled in the art. Other compositions and/or components that may be suitably included in the kit and are also identifiable by a person skilled in the art.

The identifier and the reagent can be included in one or more compositions where the identifier and/or the reagent are included with a suitable vehicle, carrier or auxiliary agent.

In the diagnostic kits herein disclosed, the agents and identifier reagents can be provided in the kits, with suitable instructions and other necessary reagents, in order to perform the methods here disclosed. The kit will normally contain the compositions in separate containers. Instructions, for example written or audio instructions, on paper or electronic support such as tapes or CD-ROMs, for carrying out the assay, will usually be included in the kit. The kit can also contain, depending on the particular method used, other packaged reagents and materials (i.e. wash buffers and the like).

Further details concerning the identification of the suitable carrier agent or auxiliary agent of the compositions, and generally manufacturing and packaging of the kit, can be identified by the person skilled in the art upon reading of the present disclosure.

The kit of parts herein disclosed can be used in particular for diagnostic purpose. As a result a non-invasive diagnostic detection of pathologies, diseases or disorder and in particular of oral cavity and oropharyngeal cancer in patients, is disclosed.

The use of the fluid phase of saliva has unique advantages over the use of exfoliated cells. Depending on the location of the tumor, one may not be able to easily access and swab the tumor bed. Although salivary biomarkers could not identify the site from which the tumor originated, they could identify patients at risk. Such a saliva test could be administered by nonspecialists in remote locations as a screening tool to select patients for referral for careful evaluation of the upper aerodigestive tract. Finding early stage, previously undetected disease may ultimately save lives. Moreover, the use of easily accessible biomarkers may prove highly beneficial in large populations or chemoprevention trials. This could be envisioned during routine dental visits or targeted screening of individuals at high risk of development of the disease. A home test kit can also be envisioned.

Also the use of blood test is envisioned in particular for cancer early detection. Recovering the cell-free circulating mRNA or protein biomarkers in the serum of cancer patients representing characteristics of tumor genetic alteration, such as IL6 mRNA and protein, H3F3A, mRNA TPT1 mRNA, FTH1 mRNA, NCOA4 mRNA and ARCR mRNA diagnostic for OSCC, could be envisioned as a screening test for presence of occult OSCC during routine physician's visit with blood work or targeted screening of individuals at high risk for oral cancer development. A home test kit can also be envisioned, including preferably In particular, peripheral blood can be obtained from subjects using routine clinical procedures, and mRNA and proteins can be isolated, preferably with an optimized procedures herein disclosed. Real time quantitative PCR and ELISA for the respective cytokine will be performed for one or biomarkers, such as IL6.

A perspective embodiments of the methods herein disclosed are directed towards the eventual creation of micro-/nano-electrical mechanical systems (MEMS/NEMS) for the ultrasensitive detection of molecular biomarkers in oral fluid. RNA and protein expression for the validated OSCC biomarkers will be selected as targets for cancer detection. The integration of these detection systems for the concurrent detection of mRNA and protein for multiple OSCC biomarkers will result in an efficient, automated, affordable system for oral fluid based cancer diagnostics.

Further details concerning reagents, conditions, compositions techniques to be used in the method and kits of the disclosure are identifiable by a person skilled in the art upon reading of the present disclosure.

Also appropriate modifications of the STD methods and kits herein disclosed and exemplified as associated to OSCC and/or HSNCC, for the mRNA profiling and transcriptome analysis associated with investigation and diagnosis of other pathology diseases and disorders can be made by a person skilled in the art upon reading of the present disclosure.

The following examples are provided to describe the invention in further detail. These examples, which set forth a preferred mode presently contemplated for carrying out the invention, are intended to illustrate and not to limit the invention

EXAMPLES

Example 1: RNA Isolation, Amplification and Gene Expression Profiling from Cell-Free Saliva of Normal Donors Normal Subjects Saliva samples were obtained from ten normal donors from the Division of Otolaryngology, Head and Neck Surgery, at the Medical Center, University of California, Los Angeles (UCLA), CA, in accordance with a protocol approved by the UCLA Institutional Review Board. The following inclusion criteria were used: age 30 years; no history of malignancy, immunodeficiency, autoimmune disorders, hepatitis, HIV infection or smoking. The study population was composed of 6 males and 4 females, with an average age of 42 years (range from 32 to 55 years).

Saliva Collection and Processing to Obtain the Relevant Fluid Phase

Unstimulated saliva were collected between 9 am and 10 am in accordance with published protocols [38]. Subjects were asked to refrain from eating, drinking, smoking or oral hygiene procedures for at least one hour prior to saliva collection. Saliva samples were centrifuged at 2,600×g for 15 min at 4° C. Saliva supernatant was separated from the cellular phase. RNase inhibitor (Superase-In, Ambion Inc., Austin, Tex., USA) and protease inhibitor (Aprotinin, Sigma, St. Louis, Mo., USA) were then added into the cell-free saliva supernatant.

RNA Isolation from Cell-Free Saliva

RNA was isolated from cell-free saliva supernatant using the modified protocol from the manufacturer (QIAamp Viral RNA kit, Qiagen, valencia, CA, USA). Saliva (560 µl), mixed well with AVL buffer (2,240 µl), was incubated at room temperature for 10 min. Absolute ethanol (2,240 µl) was added and the solution passed through silica columns by centrifugation at 6,000×g for 1 min. The columns were then washed twice, centrifuged at 20,000×g for 2 min, and eluted with 30 µl RNase free water at 9,000×g for 2 min. Aliquots of RNA were treated with RNase-free DNase (DNase I-DNA-free, Ambion Inc., Austin, Tex., USA) according to the manufacturer's instructions.

The stability of the isolated RNA was examined by RT-PCR typing for actin-β (ACTB) after storage for 1, 3, and 6 months. The results reported on FIG. 1A show that the mRNA isolated could be preserved without significant degradation for more than 6 month at −80° C.

The quality of isolated RNA was examined by RT-PCR for three house-keeping gene transcripts: glyceraldehyde-3-phosphate dehydrogenase (GAPDH), actin-β (ACTB) and ribosomal protein S9 (RPS9). Primers were designed using PRIMER3 software (http://www.genome.wi.mit.edu) and were synthesized commercially (Fisher Scientific, Tustin, Calif., USA) as follows: the primers having the sequence reported attached sequence listing as SEQ ID NO: 1 and SEQ ID NO: 2 for GAPDH; the primers having the sequence reported attached sequence listing as SEQ ID NO: 3 and SEQ ID NO: 4 for ACTB; the primers having the sequence reported attached sequence listing as SEQ ID NO: 5 and SEQ ID NO: 6 for RPS9. The quantity of RNA was estimated using Ribogreen® RNA Quantitation Kit (Molecular Probes, Eugene, Oreg., USA). The results are shown in FIG. 1B, wherein GAPDH (B1), RPS9 (B2) and ACTB (B3) were detected consistently in all 10 cases tested, demonstrating that all 10 saliva samples contain mRNAs that encode for house keeping genes: GAPDH, ACTB and RPS9.

The mRNA of these genes could be preserved without significant degradation for more than 6 months at −80° C., (see results for ACTB reported on FIG. 1A).

Target CRNA Preparation

Isolated RNA was then subjected to linear amplification according to published method from our laboratory (Ohyama et al., 2000). In brief, reverse transcription using T7-oligo-(dT)24 as the primer was performed to synthesize the first strand cDNA. The first round of in vitro transcription (IVT) was carried out using T7 RNA polymerase (Ambion Inc., Austin, Tex., USA). The BioArray™ High Yield RNA Transcript Labeling System (Enzo Life Sciences, Farmingdale, N.Y., USA) was used for the second round IVT to biotinylate the cRNA product; the labeled cRNA was purified using GeneChip® Sample Cleanup Module (Affymetrix, Santa Clara, Calif., USA).

Figure 2:
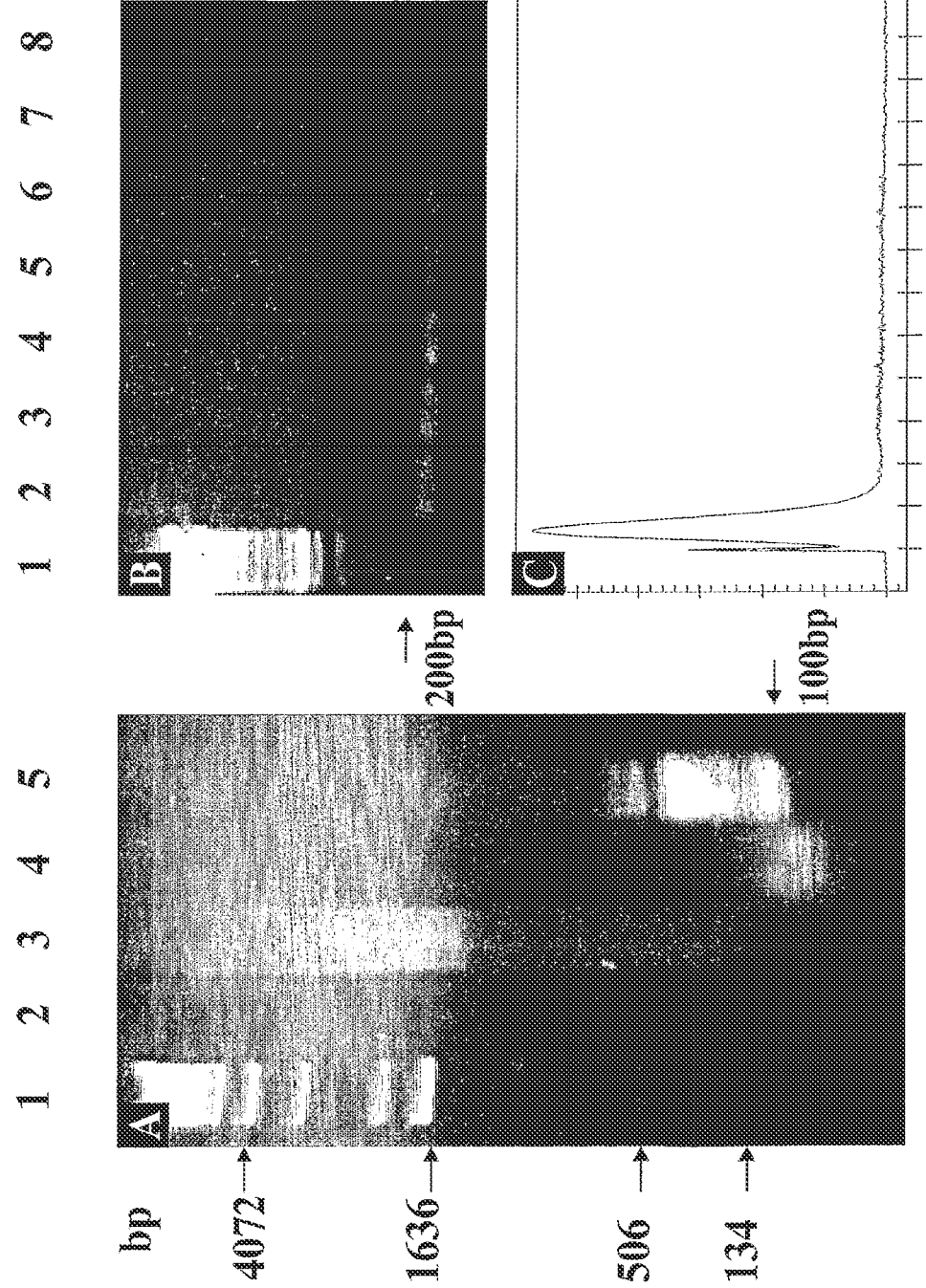
FIG. 2A shows results of a capillary electrophoresis performed to monitor RNA amplification from RNA isolated from cell-free saliva supernatant from human beings. Lanes 1 to 5 show 1 kb DNA ladder (lane 1), 5 µl saliva after RNA isolation (undetectable) (lane 2), 1 µl two round amplified cRNA (range from 200 bp to ~4 kb) (lane 3), 1 µl cRNA after fragmentation (around 100 bp) (lane 4) and Ambion RNA Century Marker (lane 5). A molecular size marker is indicated on the left side and right side of the Figure by arrows.
FIG. 2B shows results of a PCR performed on RNA isolated from cell-free saliva supernatant from human beings at various stage of amplification and typing for ACTB. Lane 1 to 8 shows 100 bp DNA ladder (lane 1), total RNA isolated from cell-free saliva (lane 2), 1st round cDNA (lane 3), 1st round cRNA after RT (lane 4), 2nd round cDNA (lane 5), 2nd round cRNA after RT (lane 6), positive control (human total RNA, BD Biosciences Clontech, Palo Alto, Calif., USA) (lane 7) and negative control (omitting templates) (lane 8). A molecular size marker is indicated on the left side of the Figure by arrows.
FIG. 2C shows a diagram reporting results of the analysis of target cRNA performed by Agilent 2100 bioanalyzer before hybridization on microarray. On x axis, the molecular weight (bp) of the fragmented cRNA with reference to the marker RNA, is indicated. On y axis, the quantity of the fragmented cRNA (ug/ml) measurable by a Bioanalyzer, is indicated.

The quantity and quality of cRNA were determined by spectrophotometry and gel electrophoresis. Exemplary results of agarose gel electrophoresis test reported on FIG. 2A show different quantities of amplified cRNA at the different stages of the RNA amplification.

Also small aliquots from each of the isolation and amplification steps were used to assess the quality by RT-PCR. Exemplary results reported in FIG. 2B show PCR typing ACTB performed at the various stages of RNA amplification, wherein the expected single band (153 bp) can be detected in every main step of the salivary RNA amplification process.

The quality of the fragmented cRNA (prepared as described by Kelly, 2002) was also assessed by capillary electrophoresis using the 2100 Bioanalyzer (Agilent Technologies, Palo Alto, Calif., USA). Exemplary results reported in FIG. 2C show one single peak in a narrow range (50-200 bp) demonstrating proper fragmentation.

Gene Expression Profiling in the Targeted cRNA Preparation

Gene expression profiling was performed in cell free-saliva obtained from ten normal donors, wherein on average, 60.5±13.1 ng (n=10) of total RNA was obtained from 560 µl cell-free saliva samples. The results are reported on Table 1.

TABLE 1

| Subject | Gender | Age | RNA (ng)a | cRNA (~tg)' ~ | Present Probesc | Probe ~%" |
|---|---|---|---|---|---|---|
| 1 | F | 53 | 60.4 | 44.3 | 3172 | 14.24 |
| 2 | M | 42 | 51.6 | 40.8 | 2591 | 11.62 |
| 3 | M | 55 | 43.2 | 34.8 | 2385 | 10.70 |
| 4 | M | 42 | 48.2 | 38.0 | 2701 | 12.12 |
| 5 | M | 46 | 60.6 | 42.7 | 3644 | 16.35 |

TABLE 1-continued

| Subject | Gender | Age | RNA (ng)a | cRNA (~tg)'~ | Present Probesc | Probe ~%" |
|---|---|---|---|---|---|---|
| 6 | M | 48 | 64.8 | 41.8 | 2972 | 13.34 |
| 7 | F | 40 | 75.0 | 44.3 | 2815 | 12.63 |
| 8 | M | 33 | 77.8 | 49.3 | 4159 | 18.66 |
| 9 | F | 32 | 48.8 | 41.4 | 2711 | 12.17 |
| 10 | F | 32 | 79.8 | 44.4 | 4282 | 19.22 |
| Mean ± SD | | 42 ± 8.3 | 60.5 ± 13.12 | 42.2 ± 3.94 | 3143 ± 665.0 | 14.11 ± 2.98 |

The total RNA quantity is the RNA in 560 µL cell-free saliva supernatant; the cRNA quantity is after two rounds of T7 amplification. Number of probes showing present call on HG U133A microarray (detection p<0.04). Present percentage (P %)=Number of probes assigned present call/Number of total probes (22,283 for HG U133A microarray).

After two rounds of T7 RNA linear amplification, the average yield of biotinylated cRNA was 42.2±3.9 µg with A260/280=2.067±0.082 (Table 1). The cRNA ranged from 200 bp to 4 kb before fragmentation; and was concentrated to approximately 100 bp after fragmentation. The quality of cRNA probe was confirmed by capillary electrophoresis before the hybridizations. ACTB mRNA was detectable using PCR/RT-PCR on original sample and products from each amplification steps: first cDNA, first In Vitro Transcription (IVT), second cDNA and second IVT, with a resulting agarose electrophoresis pattern comparable to the one shown in FIG. 2B.

Example 2: Microarray Profiling of mRNA from Cell-Free Saliva of Normal Donors

Saliva was collected processed and the RNA isolated as reported in Example 1. Also, stability, quality and quantity of the RNA was assessed are reported in Example 1.
HG-U1331A Microarray Analysis The Affymetrix Human Genome U133A Array, which contains 22,215 human gene cDNA probe sets representing ~19,000 genes (i.e., each gene may be represented by more than one probe sets), was applied for gene expression profiling. The array data were normalized and analyzed using Microarray Suite (MAS) software (Affymetrix). A detection p-value was obtained for each probe set. Any probe sets with p<0.04 was assigned "present", indicating the matching gene transcript is reliably detected (Affymetrix, 2001). The total number of present probe sets on each array was obtained and the present percentage (P %) of present genes was calculated. Functional classification was performed on selected genes (present on all ten arrays, p<0.01) by using the Gene Ontology Mining Tool (www.netaffx.com).

Salivary mRNA profiles of ten normal subjects were obtained using HG U133A array contains 22,283 cDNA probes. An average of 3,143±665.0 probe sets (p<0.04) was found on each array (n=10) with assigned present calls. These probe sets represent approximately 3,000 different mRNAs. The average present call percentage was 14.11±2.98% (n=10). A reference database which includes data from the ten arrays was generated. The probe sets representing GAPDH, ACTB and RPS9 assigned present calls on all 10 arrays. There were totally 207 probe sets representing 185 genes assigned present calls on all 10 arrays with detection p<0.01. These 10 genes were categorized on the basis of their known roles in biological processes and molecular functions. Biological processes and molecular functions of 185 genes in cell-free saliva from ten normal donors (data obtained by using Gene Ontology Mining Tool) are reported on Table 2.

TABLE 2

| | Genes, nb |
|---|---|
| Biological process[a] | |
| Cell growth and/or maintenance | 119 |
| Metabolism | 93 |
| Biosynthesis | 70 |
| Protein metabolism | 76 |
| Nucleotide metabolism | 10 |
| Other metabolisms | 18 |
| Cell organization and biogenesis | 2 |
| Homeostasis | 3 |
| Cell cycle | 5 |
| Cell proliferation | 11 |
| Transport | 5 |
| Cell motility | 8 |
| Cell communication | 34 |
| Response to external stimulus | 19 |
| Cell adhesion | 3 |
| Cell-cell signaling | 5 |
| Signal transduction | 17 |
| Obsolete | 8 |
| Development | 18 |
| Death | 2 |
| Biological process unknown | 11 |
| Molecular function[a] | |
| Binding | 118 |
| Nucleic acid binding | 89 |
| RNA binding | 73 |
| Calcium ion binding | 12 |
| Other binding | 23 |
| Structural molecule | 95 |
| Ribosomal constituent | 73 |
| Cytoskeleton constituent | 17 |
| Muscle constituent | 2 |
| Obsolete | 15 |
| Transporter | 4 |
| Enzyme | 20 |
| Signal transduction | 10 |
| Transcription regulator | 7 |
| Translation regulator | 5 |
| Enzyme regulator | 9 |
| Cell adhesion molecule | 1 |
| Molecular function unknown | 6 |

One gene may have multiple molecular functions or participate in different biological processes. Number of genes classified into a certain group/subgroup. The major functions of the 185 genes are related to cell growth/maintenance (119 genes), molecular binding (118 genes) and cellular structure composition (95 genes). We termed these 185 genes as "Normal Salivary Core Transcriptome (NSCT)".

Example 3: Q-PCR Validation and Quantitation Analysis of Microarray Profiling from Cell-Free Saliva of Normal Donors The Microarray analysis performed in Example 2 was validated through a quantitative gene expression analysis by Q-PCR Quantitative Gene Expression Analysis Q-PCR Real time quantitative PCR (Q-PCR) was used to validate the presence of human mRNA in saliva by quantifying selected genes from the 185 "Normal Salivary Core Transcriptome" genes detected by the Microarray profiling reported in Example 2. Genes ILA B, SFN and K-ALPHA-1, which were assigned present calls on all 10 arrays, were randomly selected for validation.

Q-PCR was performed using iCycler™ thermal Cycler (Bio-Rad, Hercules, Calif., USA). A 2 µl aliquot of the isolated salivary RNA (without amplification) was reverse transcribed into cDNA using MuLV Reverse Transcriptase (Applied Biosystems, Foster City, Calif., USA). The resulting cDNA (3 µl) was used for PCR amplification using iQ SYBR Green Supermix (Bio-Rad, Hercules, Calif., USA). The primers were synthesized by Sigma-Genosys (Woodlands, Tex., USA) as follows: the primers having the sequence reported attached sequence listing as SEQ ID NO: 7 and SEQ ID NO: 8 for interleukin 1, beta (IL1B); the primers having the sequence reported attached sequence listing as SEQ ID NO:9 nd SEQ ID NO: 10 for stratifin (SFN); the primers having the sequence reported attached sequence listing as SEQ ID NO: 11 and SEQ ID NO: 12 for tubulin, alpha, ubiquitous (K-ALPHA-1). All reactions were performed in triplicate with conditions customized for the specific PCR products. The initial amount of cDNA of a particular template was extrapolated from a standard curve using the LightCycler software 3.0 (Bio-Rad, Hercules, Calif., USA). The detailed procedure for quantification by standard curve has been previously described (Ginzinger, 2002).

Q-PCR results showed that mRNA of IL1B, SFN and K-ALPHA-1 were detectable in all 10 original, unamplified, cell-free saliva. The relative amounts (in copy number) of these transcripts (n=10) are: $8.68 \times 10^3 \pm 4.15 \times 10^3$ for IL1B; $1.29 \times 10^5 \pm 1.08 \times 10^5$ for SFN; and $4.71 \times 10^6 \pm 8.37 \times 10^5$ for K-ALPHA-1. The relative RNA expression levels of these genes measured by Q-PCR were similar to those measured by the microarrays (data not shown).

Example 4: IL6 and IL8 mRNA Isolation Amplification and Analysis of the Expression in Cell-Free Saliva of OSCC Patients Patients Selection Patients were recruited from the Division of Head and Neck Surgery at the University of California, Los Angeles (UCLA) Medical Center, Los Angeles, Calif.; the University of Southern California (USC) Medical Center, Los Angeles, Calif.; and the University of California San Francisco (UCSF) Medical Center, San Francisco, Calif., over a 6-month period.

Thirty-two patients with documented primary T1 or T2 squamous cell carcinoma of the oral cavity (OC) or oropharynx (OP) were included in this study. All patients had recently been diagnosed with primary disease, and had not received any prior treatment in the form of chemotherapy, radiotherapy, surgery, or alternative remedies. An equal number of age and sex matched subjects with comparable smoking histories were selected as a control comparison group.

Among the two subject groups, there were no significant differences in terms of mean age (standard deviation, SD): OSCC patients, 49.3 (7.5) years; normal subjects, 48.8 (5.7) years (Student's t test P>0.80); gender (Student's t test P>0.90); or smoking history (Student's t test P>0.75). No subjects had a history of prior malignancy, immunodeficiency, autoimmune disorders, hepatitis, or HIV infection. Each of the individuals in the control group underwent a physical examination by a head and neck surgeon, to ensure that no suspicious mucosal lesion was present.

Saliva Collection and Processing

Informed consent had been given by all patients. Saliva and serum procurement procedures were approved by the institutional review board at each institution: the University of California, Los Angeles (UCLA); the University of Southern California (USC); and the University of California San Francisco (UCSF).

Saliva from 32 patients with OC or OP SCCA, and 32 unaffected age- and gender-matched control subjects were obtained for a prospective comparison of cytokine concentration.

The subjects were required to abstain from eating, drinking, smoking, or using oral hygiene products for at least one hour prior to saliva collection. Saliva collection was performed using the "draining (drooling)" method of Navazesh and Christensen,[7] for a total donation of 5 cc saliva. Saliva samples were subjected to centrifugation at 3500 rpm (2600×g) for 15 minutes at 4° C. by a Sorvall RT6000D centrifuge (DuPont, Wilmington, Del.). The fluid-phase was then removed, and RNAse (Superase-In, RNAse Inhibitor, Ambion Inc., Austin, Tex.) and protease (Aprotinin, Sigma, St. Louis, Mo.; Phenylmethylsulfonylfluoride, Sigma, St. Louis, Mo.; Sodium Orthovanadate, Sigma, St. Louis, Mo.) inhibitors were then added promptly on ice. The conditions for the separation of the cellular and fluid phases of saliva were optimized to ensure no mechanical rupture of cellular elements which would contribute to the mRNA detected in the fluid phase. All samples were subsequently treated with DNAse (DNAseI-DNA-free, Ambion Inc., Austin, Tex.). The cell pellet was retained and stored at −80° C.

RNA Isolation from Cell-Free Saliva

560 µl of saliva supernatant were then processed using the QIAamp Viral RNA mini kit (QIAGEN, Chatsworth, Calif.) kit. RNA was extracted according to the manufacturer's instructions. Samples were air-dried and resuspended in water treated with diethyl pyrocarbonate and were kept on ice for immediate usage or stored at −80° C. Aliquots of RNA were treated with RNAse-free DNAse (DNAseI-DNA-free, Ambion Inc., Austin, Tex.) according to the manufacturer's instructions. Concentrations of RNA were determined spectrophotometrically, and the integrity was checked by electrophoresis in agarose gels containing formaldehyde.

Reverse Transcriptase-Polymerase Chain Reaction

Presence of IL6 and IL8 mRNA transcripts in the fluid phase in saliva was tested by using reverse transcriptase-polymerase chain reaction (RT-PCR).

RNA from each sample was reverse-transcribed in 40 µl of reaction mixture containing 2.5 U of Moloney murine leukemia virus reverse transcriptase (Applied Biosystems Inc. (ABI, Foster City, Calif.) and 50 pmol of random hexanucleotides (ABI, Foster City, Calif.) at 42° C. for 45 minutes. Based on the published sequences, oligonucletide primers were synthesized commercially at Fisher Scientific (Tustin, Calif.) for PCR as follows: the primers having the sequence reported attached sequence listing as SEQ ID NO: 13 and SEQ ID NO: 14 for β-actin; the primers having the sequence reported attached sequence listing as SEQ ID NO: 15 and SEQ ID NO: 16 for IL8; and the primers having the sequence reported attached sequence listing as SEQ ID NO: 17 and SEQ ID NO: 18 for IL6.

Amplification of the complementary DNA (cDNA) was carried out using 50 cycles at 95° C. for 20 seconds, 60° C. for 30 seconds, and 72° C. for 30 seconds; followed by a final extension cycle of 72° C. for 7 minutes. Specificity of the PCR products was verified by the predicted size and by restriction digestion. To establish the specificity of the responses, negative controls were used in which input RNA was omitted or in which RNA was used but reverse transcriptase omitted. As a positive control, mRNA was extracted from total salivary gland RNA (Human Salivary Gland Total RNA, Clontech, Palo Alto, Calif.). To ensure RNA quality, all preparations were subjected to analysis of expression.

Figure 3:
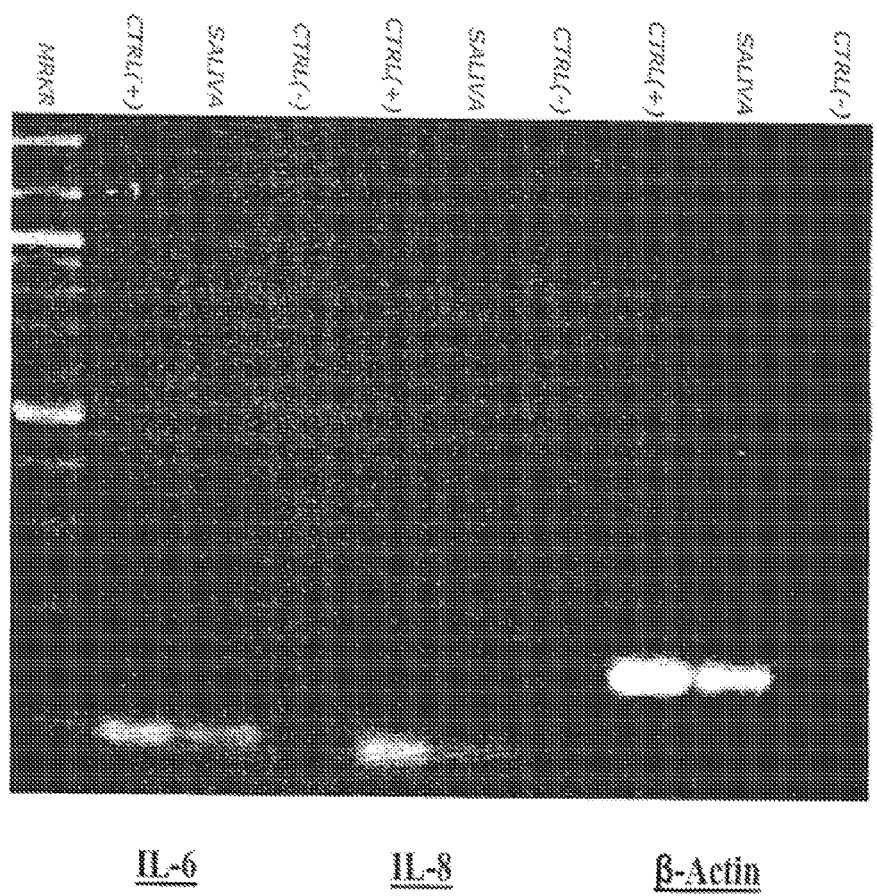
FIG. 3 shows results of a RT-PCR performed on RNA isolated from cell-free saliva supernatant from human beings (saliva) together with a ladder (Mrkr) positive controls (Ctrl(+)) and negative controls (Ctrl(−)) and typing for IL6 (IL6), IL8 (IL8) and β-Actin (β-Actin).

The RT-PCR studies so performed showed that saliva and serum contained mRNA encoding for IL6 and IL8. Exemplary results reported in FIG. 3, show PCR products of the sizes (95 bp for IL6 and 88 bp for IL8) that were expected from the selected primers. The same-sized products were expressed in the positive control.

Figure 4:
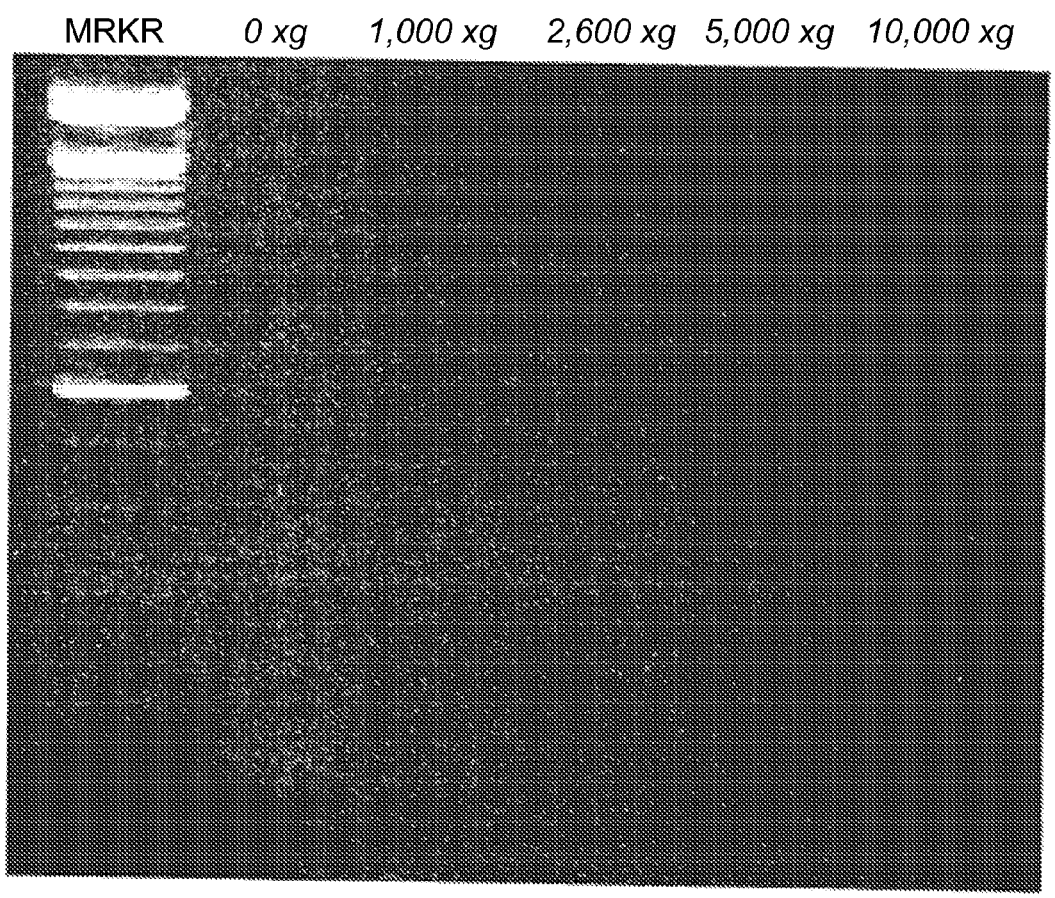
FIG. 4 shows results of a PCR performed for the housekeeping β-actin on whole saliva, serum samples, and samples that had been centrifuged at 0×g (0×g), 1,000×g (1,000×g), 2,600×g (2,600×g), 5,000×g (5,000×g) and 10,000×g (10,000×g) using genomic DNA as marker (Mrkr) for cell lysis and spillage of intracellular compounds.

In order to ensure that the RNA and protein analyzed were from the fluid phase of saliva only and to ensure the lack of contamination by intracellular components, the centrifugation speed for the saliva samples was optimized. PCR for the housekeeping genes p-actin and ubiquitin on whole saliva samples, and samples that had been centrifuged at various speeds using DNA as a marker of cell lysis and spillage of intracellular components. The results support an optimal centrifugation speed for saliva samples of 2,600±52×g, with a preferred speed of 2,600 ×g (see exemplary results reported on FIG. 4)

Example 5: IL6 and IL8 mRNA Isolation, Amplification and Analysis of the Expression in Serum of OSCC Patients Patients recruited as reported in Example 4, where subjected to analysis of presence of IL6 and IL8 mRNA in blood serum.

Serum Collection and Processing

Serum from 19 patients with OC or OP SCCA, and 32 unaffected age- and gender-matched control subjects were obtained for a prospective comparison of cytokine concentration. Among the subject groups, there were no significant differences in terms of age, gender, alcohol consumption, or smoking history (P>0.75).

Blood was drawn from control subjects and patients prior to treatment. Sera were collected by centrifuging whole blood at 3000 rpm (1000×g) for 10 minutes at 15° C. by a Sorvall RT6000D centrifuge (DuPont, Wilmington, Del.). Serum was then separated, and RNAse (Superase-In, RNAse Inhibitor, Ambion Inc., Austin, Tex.) and protease (Aprotinin, Sigma, St. Louis, Mo.; Phenylmethylsulfonylfluoride, Sigma, St. Louis, Mo.; Sodium Orthovanadate, Sigma, St. Louis, Mo.) inhibitors were then added promptly on ice. All samples were subsequently treated with DNAse (DNAseI-DNA-free, Ambion Inc., Austin, Tex.). The aliquots were stored at −80° C. until further use.

Reverse Transcriptase-Polymerase Chain Reaction

Presence of IL6 and IL8 mRNA transcripts in the serum was tested by using reverse transcriptase-polymerase chain reaction (RT-PCR) performed as described in Example 4 above.

The RT-PCR studies so performed showed that serum contained mRNA encoding for IL6 and IL8, with electrophoresis gel pattern comparable to the one shown in FIG. 3.

In order to ensure that the RNA and protein analyzed were from the fluid phase of serum only and to ensure the lack of contamination by intracellular components, the centrifugation speed for the serum samples was optimized following the same approach described in Example 4 for saliva samples. The results support an optimal centrifugation speed for saliva samples of 1,000±20 ×g with a preferred speed of 1,000 ×g.

Example 6: IL6 and IL8 Cytokine Levels Analysis in Saliva From OSCC Patients On demonstrating that IL6 and IL8 mRNA transcripts were present in the fluid phase in saliva, we prospectively examined and compared the levels of IL6 and IL8 in the saliva of unaffected subjects and patients with OSCC using quantitative real time PCR (qRT-PCR) and ELISA.

Saliva from 32 patients with OSCC, and 32 age- and gender-matched control subjects were obtained. Among the subject groups, there were no significant differences in terms of age, gender, alcohol consumption, or smoking history (P>0.75).

Real Time PCR for Quantification of IL6 and IL8 mRNA Concentrations in Saliva from Patients and Normal Subjects To analyze quantitatively the result of RT-PCR, quantitative real-time PCR (Bio-Rad iCycler, Thermal Cycler, Bio-Rad Laboratories, Hercules, Calif.) was used. Each sample was tested in triplicate. The amplification reactions were carried out in a 20 µl mixture, using iQ SYBR Green Supermix (Bio-Rad Laboratories, Hercules, Calif.). After initial denaturation at 95° C. for 3 minutes, 50 PCR cycles were performed at 60° C. for 20 seconds, then 20 seconds at 72° C., then 20 seconds at 83° C., followed by 1 minute at 95° C., then followed by a final 1 minute extension at 55° C. Aliquots were taken from each well and checked by electrophoresis in agarose gels in order to ensure the specificity of the products.

Figure 5A:
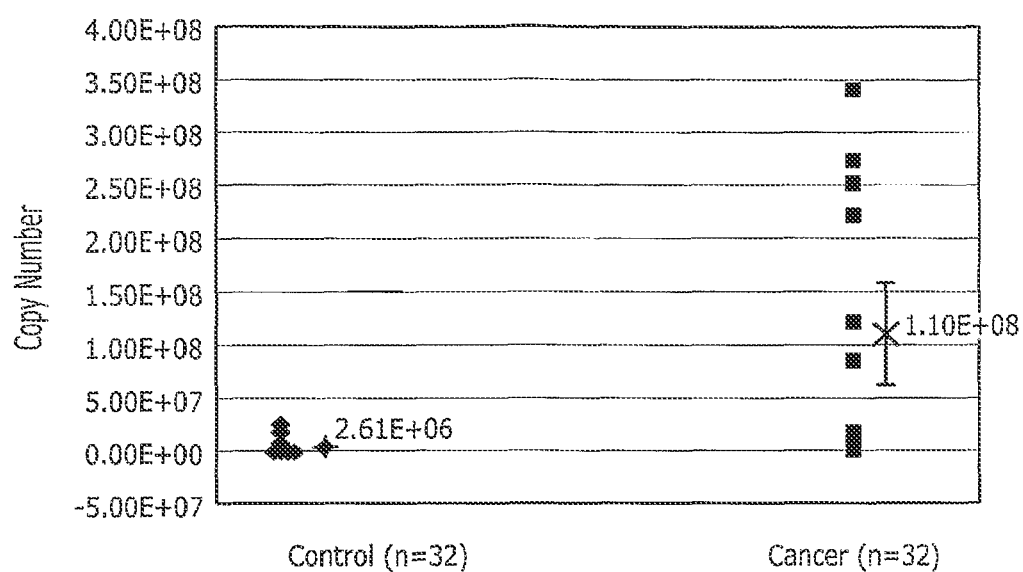
FIG. 5A shows a diagram reporting the mean concentrations of mRNA for IL8 detected in replicate samples by qRT-PCR in saliva from patients with OSCC (Cancer) and normal subjects (Control). On x axis the sample groups are reported. On y axis the number of copies detected is reported.

The RT-PCR results are illustrated by the diagram shown in FIG. 5 A. Such results show that IL8 at both the mRNA and protein levels, was detected in higher concentrations in the saliva of patients with OSCC when compared with control subjects (t test, P<0.01). There was a significant difference in the amount of IL8 mRNA expression between saliva from OSCC patients and disease-free controls. The mean copy number was $1.1 \times 10^3$ for the OSCC group, and $2.6 \times 10^1$ for the control group. The difference between the two groups was highly statistically significant (P<0.0008).

No significant differences were instead found in the salivary concentration of IL6 at the mRNA level. Within the sample size studies, the inventors were also unable to detect differences between smoking and nonsmoking subjects.

ELISA for Quantification of IL6 and IL8 Protein Concentrations in Saliva from Patients and Normal Subjects ELISA kits for IL6 and IL8 were used (Pierce Endogen, Rockford, Ill.) according to the manufacturer's protocol. Each sample was tested in duplicate in each of two replicate experiments. After development of the colorimetric reaction, the absorbance at 450 nm was quantitated by an eight channel spectrophotometer (EL800 Universal Microplate Reader, BIO-TEK Instruments Inc., Winooski, Vt.), and the absorbance readings were converted to pg/ml based upon standard curves obtained with recombinant cytokine in each assay. If the absorbance readings exceeded the linear range of the standard curves, ELISA assay was repeated after serial dilution of the supernatants. Each sample was tested in at least two ELISA experiments, and the data were calculated from the mean of tests for each sample.

Figure 5B:
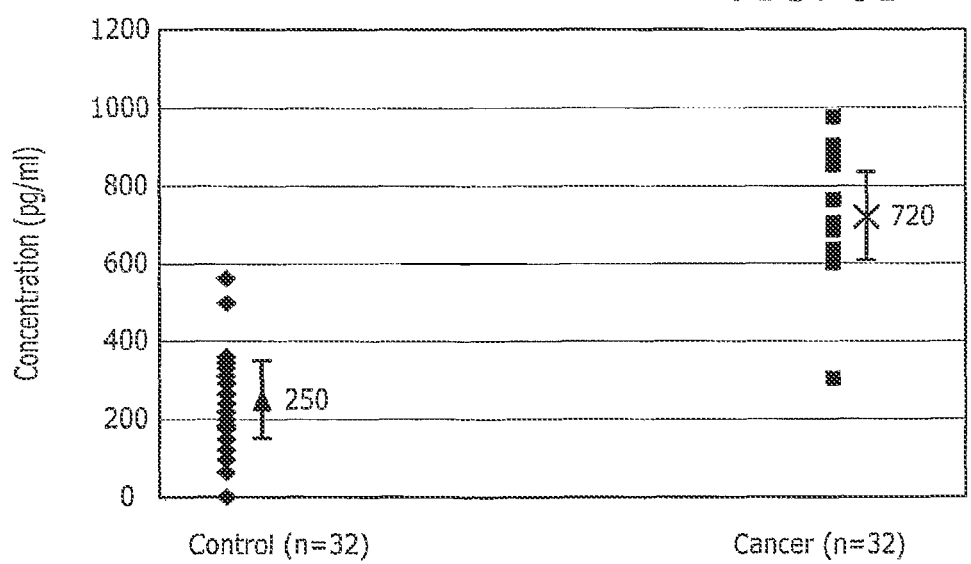
FIG. 5B shows a diagram reporting the mean concentrations of IL8 detected in replicate samples by ELISA in saliva from patients with OSCC (Cancer) and normal subjects (Control). On x axis the sample groups are reported. On y axis the concentration expressed in pg/ml, is reported.

The ELISA findings are illustrated by the diagram shown in FIG. 5B. The levels of IL8 in the saliva of OSCC patients were significantly higher (720 pg/dL) than those in the saliva of the control group (250 pg/dL) (P<0.0001). To ensure that the elevated levels of IL8 protein in saliva were not due to an elevation of total protein levels in the saliva of OSCC patients, we compared the total protein concentrations in saliva among the two groups. No significant differences were found (P>0.05).

No significant differences were found in the salivary concentration of IL6 at the protein level. Also in the ELISA analysis, no differences were detected within the sample size studies between smoking and nonsmoking subjects.

Example 7: IL6 and IL8 Cytokine Levels Analysis in Serum from OSCC Patients

We also examined and compared the levels of IL6 and IL8 in the serum of unaffected subjects and patients with OSCC using qRT-PCR and ELISA. The patients were selected as described in Example 4 and the serum processed as described in Example 5.

Real Time PCR for Quantification of IL6 and IL8 mRNA Concentrations in Serum from Patients and Normal Subjects To analyze quantitatively the result of RT-PCR, quantitative real-time PCR was performed as described in Example 6.

Figure 6A:
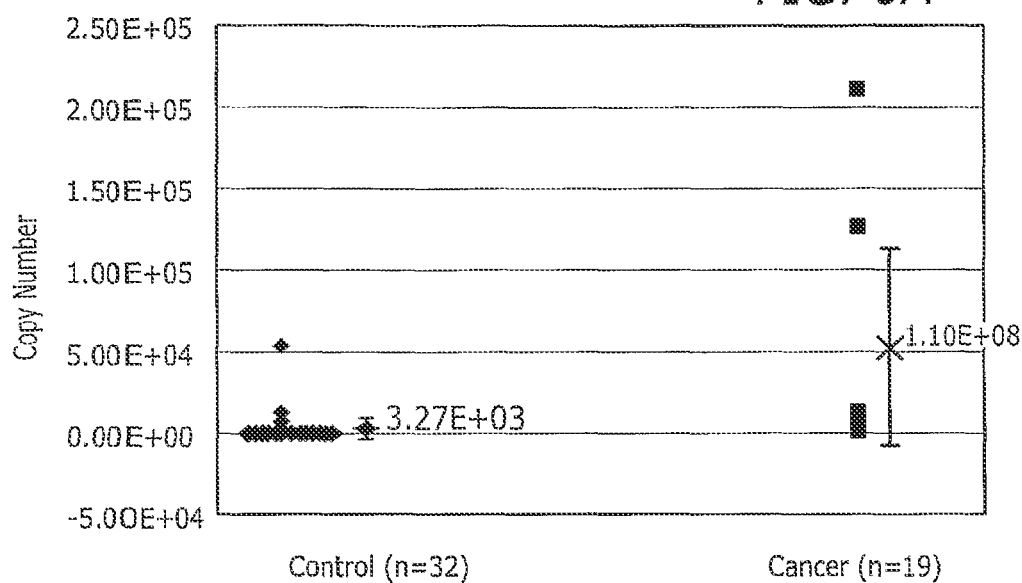
FIG. 6A shows a diagram reporting the mean concentrations of mRNA for IL6 detected in replicate samples by qRT-PCR in serum from patients with OSCC (Cancer) and normal subjects (Control). On x axis the sample groups are reported. On y axis the number of copies detected is reported.
Figure 6B:
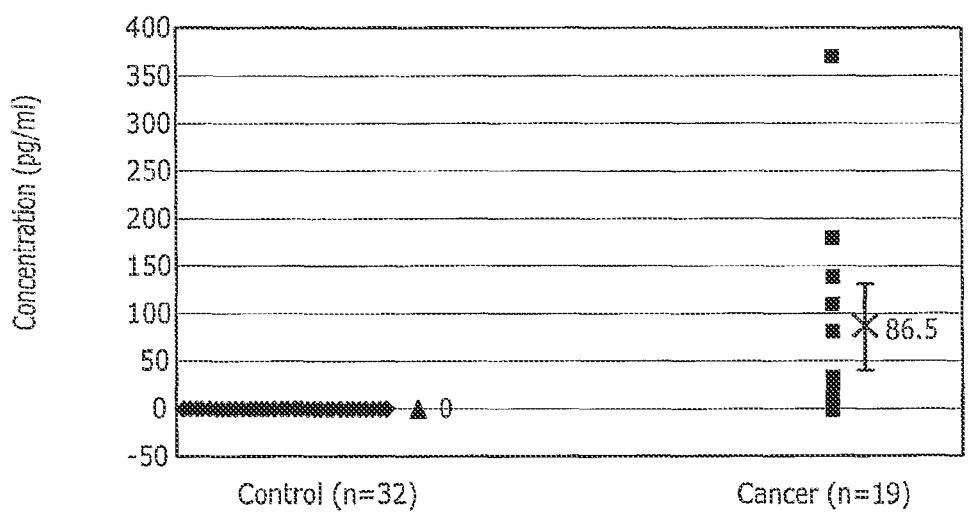
FIG. 6B shows a diagram reporting the mean concentrations of IL6 detected in replicate samples by ELISA in serum from patients with OSCC (Cancer) and normal subjects (Control). On x axis, the sample groups are reported. On y axis the concentration expressed in pg/ml, is reported

The RT-PCR results are illustrated by the diagram shown in FIG. 6 A. Such results show that IL6 at mRNA level was detected in higher concentrations in the serum of patients with OSCC when compared with control subjects (t test, P<0.001). We noted a significant difference in the amount of IL6 mRNA expression between serum from OSCC patients and disease-free controls. The mean copy number was $5.2 \times 10^4$ for the OSCC group, and $3.3 \times 10^3$ for the control group. The difference between the two groups was highly statistically significant (P<0.0004).

No significant differences were instead found in the serum concentration of IL8 at the mRNA level. Within the sample size studies, the inventors were also unable to detect differences between smoking and nonsmoking subjects.

ELISA for Quantification of IL6 and IL8 Protein Concentrations in Serum from Patients and Normal Subjects ELISA tests for quantification of IL6 and IL8 protein concentrations in serum were performed as described in Example 6.

The relevant ELISA findings are illustrated by the diagram shown in FIG. 6 B. The mean levels of IL6 in the serum of OSCC patients were significantly higher (87 pg/dL) than those in the serum of the control group (0 pg/dL) (P<0.0001).

No significant differences were found in the serum concentration of IL8 at the protein level. Also in the ELISA analysis, no differences were detected within the sample size studies between smoking and nonsmoking subjects.

Example 8: ROC and Sensitivity/Specificity Analysis

Statistical analysis of the data collected in outcome of the experiments reported on Examples 1 to 7 above demonstrates the specificity and sensitivity of these biomarkers for HNSCC, and their predictive value.

Statistical Analysis

The distributions of patient demographics were calculated overall and separately for OSCC cases and controls, and were compared between the two arms with either the Student's t-test for continuous measures or two-by-two Chi-square tables for categorical measures. The distributions of IL6 and IL8 levels in saliva and serum were computed and compared between the OSCC cases and controls using two independent group t-tests. Differences were considered significant for P values less than 0.01. Due to the range of the IL6 and IL8 levels, log transformations of these measures were also used in the analyses. Data were expressed as the mean±SD. Age, gender, and smoking history were controlled at the group level in the experimental design; these patient factors were also adjusted in the analyses when comparing IL6 and IL8 through regression modeling.

Using the binary outcome of the disease (OSCC cases) and non-disease (controls) as dependent variables, logistic regression models were fitted to estimate the probability of developing OSCC as a function of each of the potential biomarkers (IL6 or IL8), controlling for patient age, gender, and smoking history. Using the fitted logistic models, receiver operating characteristic (ROC) curve analyses were conducted to evaluate the predictive power of each of the biomarkers[8][9][10]. Through the ROC analyses, we calculated sensitivities and specificities by varying the criterion of positivity from the least (cut at probability of 0) to the most stringent (cut at probability of 1). The optimal sensitivity and specificity was determined for each of the biomarkers, and the corresponding cutoff/threshold value of each of the biomarkers was identified. The biomarker that has the largest area under the ROC curve was identified as having the strongest predictive power for detecting OSCC.

Clinical Data

The mean (SD) age of the patients with OSCC was 49.3 (7.5) years (range, 42-67 years) vs. 48.8 (5.7) years (range, 40-65 years) in the control group; (Student's t test P>0.80). Among the two subject groups, there were no significant differences in terms of age (mean age): OSCC patients, 49.3 years; normal subjects, 48.8 years (Student's t test P>0.80); gender (Student's t test P>0.90); or smoking history (Student's t test P>0.75).

ROC (Receiver Operating Characteristic) curves, plots of sensitivities versus 1-specificities, were generated for each of the potential biomarkers. Age, gender, and smoking history were controlled as described above. The areas under the ROC curves were calculated, as measures of the utility of each biomarker for detecting OSCC.

Figure 7A:
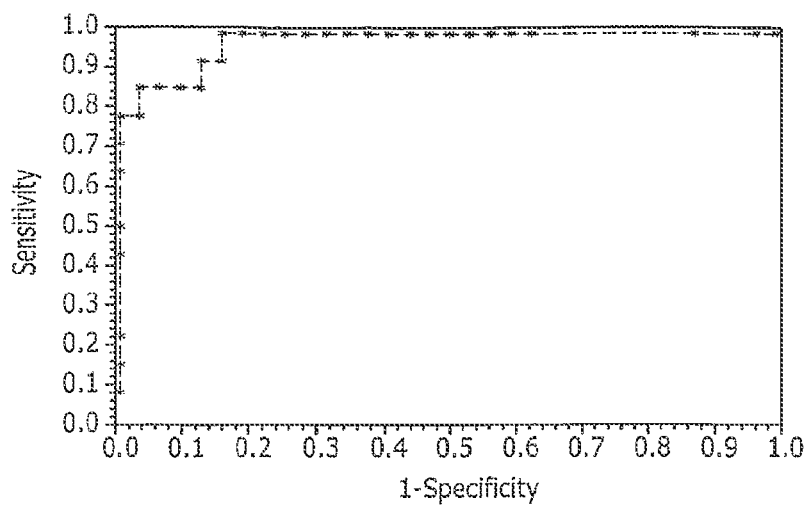
FIG. 7A shows a diagram reporting the Receiver Operating Characteristic (ROC) curve calculated for IL8 in Saliva. On the x axis 1-specificity is reported. On y axis the sensitivity is reported.
Figure 7B:
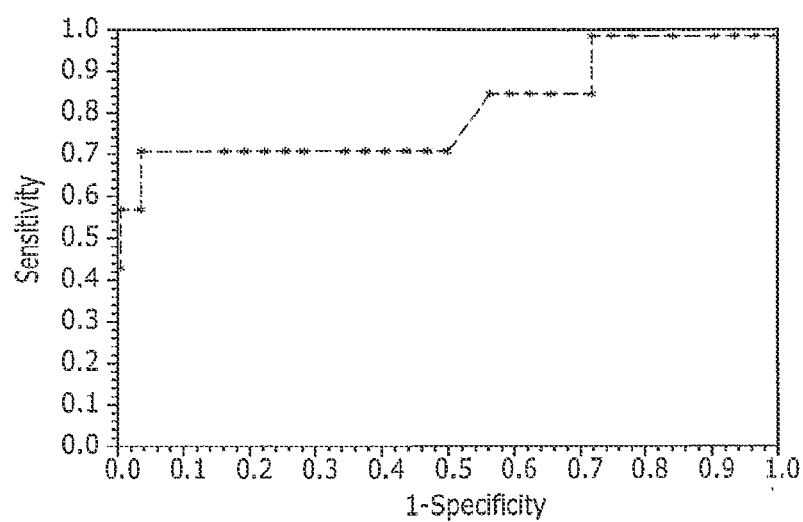
FIG. 7B shows a diagram reporting the ROC curve calculated for IL6 in serum. On the x axis 1-specificity is reported. On y axis the sensitivity is reported.

FIG. 7A and FIG. 7B show the ROC curves for IL8 in saliva and IL6 in serum, respectively. The calculated ROC values (for predicting OSCC) were 0.978 for IL8 in saliva; and 0.824 for IL6 in serum. Based on the distribution of sensitivities and specificities, thresholds of biomarkers were chosen for detecting OSCC. Based upon our data, for IL8 in saliva, a threshold value of 600 pg/dL yields a sensitivity of 86% and a specificity of 97%. Similarly, for IL6 in serum, a threshold value of greater than 0 pg/dL yields a sensitivity of 64% and a specificity of 81%.

Figure 7C:
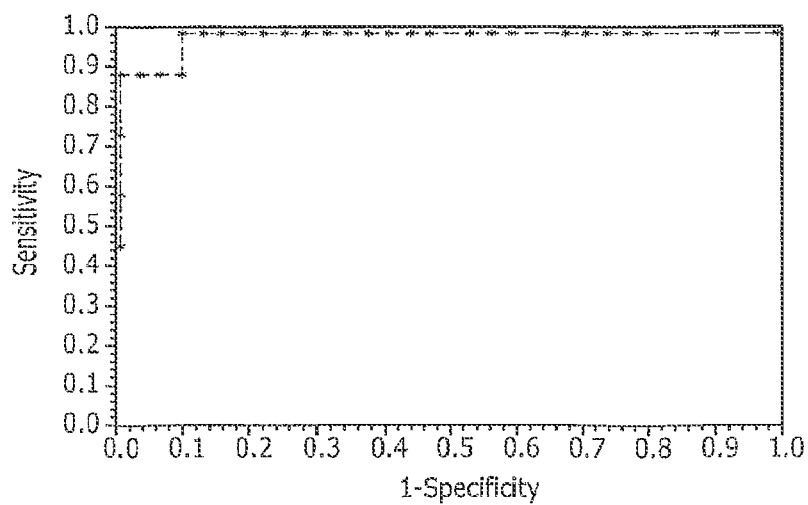
FIG. 7C shows a diagram reporting the ROC curve calculated for a combination of IL8 in saliva and IL6 in serum. On the x axis 1-specificity is reported. On y axis the sensitivity is reported.

The combination of biomarkers: IL-8 in saliva and IL-6 in serum holds great potential for OSCC diagnostics as ROC analysis yields a sensitivity of 99% and a specificity of 90% as shown in FIG. 7C.

The detailed statistics of the area under the ROC curves, the threshold values, and the corresponding sensitivities and specificities for each of the potential biomarkers in saliva and in serum are listed in Table 3.

The detailed statistics of the area under the ROC curves, the threshold values, and the corresponding sensitivities and specificities for each of the potential biomarkers in saliva and in serum are listed in Table 3 below.

TABLE 3

| Biomarker | Area under ROC | Threshold/ Cutoff | Sensitivity | Specificity |
|---|---|---|---|---|
| IL8 saliva protein | 0.978 | 600 pg/mL | 86% | 97% |
| IL6 serum protein | 0.824 | >0 pg/mL | 57% | 100% |
| IL8 saliva protein & IL6 serum protein | 0.994 | >600 pg/ml >0 p/ml | 99% | 90% |

Example 9: RNA Isolation, Amplification and Gene Expression Profiling from Serum of Oscc Patients Subject Selection Thirty-two OSCC patients were recruited from Medical Centers at University of California, Los Angeles (UCLA) and University of Southern California (USC), Los Angeles, Calif. All patients had recently been diagnosed with primary T1/T2 OSCC, and had not received any prior treatment in the form of chemotherapy, radiotherapy, surgery, or alternative remedies. Thirty-five normal donors were recruited as controls from the general population at School of Dentistry, UCLA. No subjects had a history of prior malignancy, immunodeficiency, autoimmune disorders, hepatitis, or HIV infection. All subjects signed the Institutional Review Board approved consent form agreeing to serve as blood donors for this study.

Totally sixty-seven subjects were recruited, including 32 OSCC patients and 35 normal subjects. Among the two subject groups, there were no significant differences in terms of mean age (standard deviation, SD): OSCC patients, 49.3 (7.5) years; normal subjects, 47.8 (6.4) years (Student's t test P=0.84). The gender distribution in OSCC group was 10:22 (female number/male number) and in control group was 14:21 (Chi-square test P=1). We matched the smoking history of these two groups by determining the follows. All subjects were asked: (1) For how many years had they, smoked? (2) How many packs per day had they smoked? (3) How many years had elapsed since they had quit smoking (if they had indeed quit)? (4) Did they only smoke cigarettes, or did they also use cigars, pipes, chewing tobacco, or marijuana? We then optimized the match between patients and controls in terms of the above: (1) similar pack-year history (2) similar time lapse since they had quit smoking (3) use of cigarettes exclusively. There was no significant difference between two groups in the smoking history (Student's t test P=0.77).

Blood Collection and Processing.

Blood procurement procedure was approved by the institutional review board at UCLA and USC. Blood was drawn from control subjects and patients prior to treatment. The whole blood then underwent a centrifugation by 1,000×g for 10 minutes at 15° C. by a Sorvall RT6000D centrifuge (DuPont, Wilmington, Del.). Serum was then separated, and 100 U/mL RNase inhibitor (Superase-In, Ambion Inc., Austin, Tex.) was added promptly to the serum. The aliquots were stored at −80° C. until further use.

RNA Isolation from Serum.

RNA was isolated from 560 μl serum using QIAamp Viral RNA kit (Qiagen, Valencia, Calif.). Aliquots of isolated RNA were treated with RNase-free DNase (DNaseI-DNA-free, Ambion Inc., Austin, Tex.) according to the manufacturer's instructions. The quality of isolated RNA was examined by RT-PCR for four housekeeping gene transcripts: β-actin (ACTB), β-2-microglobulin (B2M), glyceraldehyde-3-phosphate dehydrogenase (GAPDH), and ribosomal protein S9 (RPS9). Based on the published sequences, oligonucletide primers were designed and then synthesized (Sigma Genosis, Woodlands, Tex.) for PCR. RT-PCR was performed to amplify the mRNAs' coding region phenotyped in 3 segments using a common upstream primer and three different downstream primers selected from the four housekeeping gene transcripts for RT-PCR shown in Table 4.

TABLE 4

| Name | Accession no. (NCBI) | Full length (bp) | Primer sequences | Amplicon (bp) |
|---|---|---|---|---|
| ACTB | X00351 | 1761 | F: SEQ ID NO: 19 | 195 |
| | | | R1: SEQ ID NO: 20 | 705 |
| | | | R2: SEQ ID NO: 21 | 1000 |
| | | | R3: SEQ ID NO: 22 | |
| B2M | NM_004048 | 987 | F: SEQ ID NO: 23 | 216 |
| | | | R1: SEQ ID NO: 24 | 591 |
| | | | R2: SEQ ID NO: 25 | 848 |
| | | | R3: SEQ ID NO: 26 | |
| GAPDH | M33197 | 1268 | F: SEQ ID NO: 27 | 140 |
| | | | R1:SEQ ID NO: 28 | 755 |
| | | | R2: SEQ ID NO: 29 | 1184 |
| | | | R3: SEQ ID NO: 30 | |
| RPS9 | NM_001013 | 692 | F: SEQ ID NO: 31 | 188 |
| | | | R1: SEQ ID NO: 32 | 426 |
| | | | R2: SEQ ID NO: 33 | 614 |
| | | | R3: SEQ ID NO: 34 | |

In particular four serum human mRNAs were selected and coding region phenotyped in 3 segments using a common upstream primer and three different downstream primers dividing the coding region approximately into three parts. 10 μl of each PCR reaction was electrophoresed on a 2% agarose gel and stained with EtBr.

Specificity of all the PCR products was verified by the predicted size comparing the positive control (Human Salivary Gland Total RNA, Clontech, Palo Alto, Calif.). Negative controls were used in which input RNA was omitted or in which RNA was used but reverse transcriptase omitted.

Figure 8:
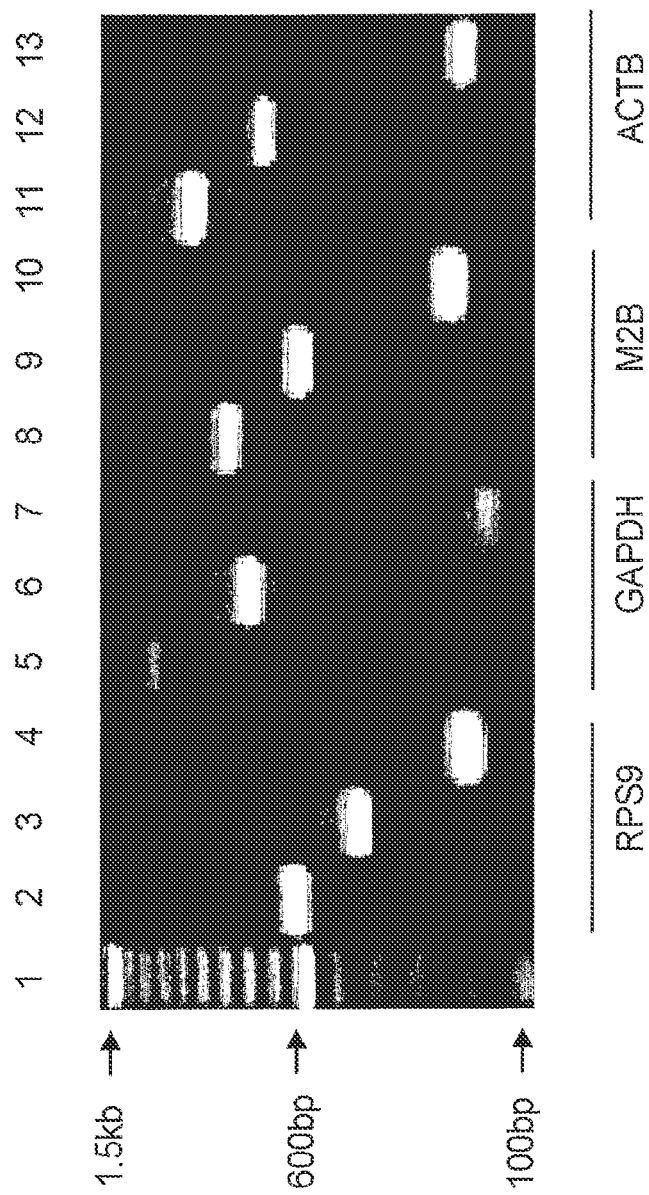
FIG. 8 shows results of a PCR reaction performed on serum human mRNA phenotyping of salivary mRNAs for RPS9 (Lane 2, 3 and 4); GAPDH (Lane 5, 6 and 7); B2M (Lane 8, 9 and 10) and ACTB (Lane 11, 12 and 13), together with DNA ladder, as a control (Lane 1).

The serum phenotype of mRNA product from human was evaluated by RT-PCR and electrophoresis. Exemplary results reported in FIG. 8, showed transcripts from four housekeeping genes (ACTB, B2M, GAPDH, and RPS9) could be detected. In particular, amplicons for RPS9 with sizes of 188, 426 and 614 bp were detected (see FIG. 8 lane 2, 3 and 4 respectively); amplicons for GAPDH with sizes of 140,755 and 1,184 bp were detected (see FIG. 8 lane 5, 6 and 7 respectively); amplicons for B2M with sizes of 216,591 and 848 bp were detected (see FIG. 8 lane 8, 9 and 10 respectively); and amplicons for ACTB with sizes of 195,705 and 1,000 bp were detected (see FIG. 8 lane 11, 12 and 13 respectively). Controls were performed even if controls data are not shown in the Figure.

The longest PCR products we amplified covered 56.8% (ACTB), 85.9% (B2M), 93.4% (GAPDH) and 88.9% (RPS9) of the full length of the corresponding mRNAs, according to the NCBI GenBank database. This result also indicated there could be intact human mRNA circulating in blood in a cell-free form.

Example 10: Microarray Profiling of mRNA of Serum from OSCC Patients

Serum from ten OSCC patients (8 male, 2 female, age=51±9.0) and from ten gender and age matched normal donors (age=49±5.6) was collected and processed as reported in Example 9 for use in microarray analysis.

Microarray Analysis

Isolated RNA from serum was subjected to linear amplification by RiboAmp™ RNA Amplification kit (Arcturus, Mountain View, Calif.). Following previously reported protocols [55], the Affymetrix Human Genome U133A Array, which contains 22,215 human gene cDNA probe sets representing ~19,000 genes (i.e., each gene may be represented by more than one probe sets), was applied for gene expression profiling.

The raw data were imported into DNA-Chip Analyzer 1.3 (dChip) software for normalization and model-based analysis [60]. dChip gives the expression index which represents the amount of mRNA/Gene expression and another parameter, called the present call of, whether or not the mRNA transcript was actually present in the sample (14). S-plus 6.0 (Insightful, Seattle, Wash.) was used for all statistical tests.

Three criteria were used to determine differentially expressed genes between OSCCs and controls. First, genes that were assigned as "absent" call in all samples were excluded. Second, a two-tailed student's t test was used for comparison of average gene expression levels among the OSCCs (n=10) and controls (n=10). The critical alpha level of 0.05 was defined for statistical significance. Third, fold ratios were calculated for those genes that showed statistically significant difference (P<0.05). Only those genes that exhibit at least 2-fold change will be included for further analysis.

The HG U133A microarrays were used to identify the difference in salivary RNA profiles between cancer patients and matched normal subjects. Among the 14,268 genes included by the previously described criteria, we identified 335 genes with P value less than 0.05 and a fold change ≥2. Among these genes, there are 223 up-regulated genes and 112 down-regulated genes in the OSCC group. According to Affymetrix, a gene that was assigned with a present call indicates this gene is reliably detected in the original sample. The number of genes that were assigned present and the present percentage on each array were shown in Table 5 reporting the human mRNA expression profiling in serum.

On average, there are 2623±868 probes in OSCC arrays and 1792±165 probes in control arrays that were assigned with present calls. OSCC group have significant more present probes than control group (P<0.002, Wilcoxon test).

Using a more stringent criterion that, for a certain gene, the present call was assigned consistently to all arrays among all cancers (n=10) or all controls (n=10), we identified 62 genes to be the candidates for further analysis. We noted that these 62 genes are all up-regulated in OSCC serum, whereas there are no genes found down-regulated using the same filtering criteria.

Example 11: Q-PCR Validation and Quantitation Analysis of Microarray Profiling from Cell-Free Saliva of OSCC Patients qPCR was performed to quantify a subset of differently expressed transcripts in saliva and to validate the microarray findings of Example 10, on an enlarged sample size including saliva from 32 OSCC patients and 35 controls.

Quantitative PCR (qPCR) Assay.

Primer sets were designed by using PRIMERS software (Table 2). Using MuLV reverse transcriptase (Applied Biosystems, Foster City, Calif.) and random hexamers as primer (ABI, Foster City, Calif.), cDNA was synthesized from the original and un-amplified serum RNA. The qPCR reactions were performed in an iCycler™ iQ real-time PCR detection system (Bio-Rad, Hercules, Calif., USA), using iQ SYBR Green Supermix (Bio-Rad, Hercules, Calif.). All reactions were performed in triplicate with customized conditions for specific products. The relative amount of cDNA/RNA of a particular template was extrapolated from the standard curve using the LightCycler software 3.0 (Bio-Rad, Hercules, Calif., USA). A two-tailed student's t test was used for statistical analysis.

Ten significant up-regulated genes: H3F3A, TPT1, FTH1, NCOA4, ARCR, THSMB (Thymosin beta 10), PRKCBI (Protein Kinase C, beta 1), FTL1 (Ferritin Light polypeptide), COX4I1 (Cytochrome c oxidase subunit IV isoform 1) and SERP1 (stress associated endoplasmic reticulum protein 1; ribosome associated membrane protein 4) were selected based on their reported cancer-association as shown in Table 6, reporting ten genes selected for qPCR validation.

TABLE 5

| | Normal | | | | OSCC | | | |
| --- | --- | --- | --- | --- | --- | --- | --- | --- |
| Subject | Gender | Age | Present Probes[a] | Probe P %[b] | Gender | Age | Present Probes[a] | Probe P %[b] |
| 1 | F | 53 | 1564 | 7.02 | F | 55 | 1990 | 8.93 |
| 2 | M | 55 | 1600 | 7.18 | M | 61 | 2924 | 13.12 |
| 3 | M | 42 | 1600 | 7.18 | M | 42 | 2126 | 9.54 |
| 4 | M | 46 | 1716 | 7.7 | M | 46 | 3316 | 14.88 |
| 5 | M | 42 | 1845 | 8.28 | M | 42 | 2937 | 13.18 |
| 6 | M | 54 | 1854 | 8.32 | M | 52 | 1794 | 8.05 |
| 7 | F | 51 | 1903 | 8.54 | F | 67 | 2119 | 9.51 |
| 8 | M | 48 | 2032 | 9.12 | M | 46 | 2019 | 9.06 |
| 9 | M | 56 | 1823 | 8.18 | M | 61 | 4646 | 20.85 |
| 10 | M | 42 | 1979 | 8.88 | M | 44 | 2362 | 10.6 |
| Mean ± SD | | 49 ± 5.6 | 1792 ± 165 | 8.04 ± 0.74 | | 51 ± 9.0 | 2623 ± 868* | 11.8 ± 3.90 |

[a]Number of probes showing present call on HG U133A microarray (detection P < 0.04).
[b]Present percentage (P %) = Number of probes assigned present call/Number of total probes (22,283 for HG U133A microarray).
*The arrays for OSCC have significant more probes assigned with present call than those for control group (P ≤ 0.002, Wilcoxon test).

TABLE 6

| Probe set ID (HG U133A) | Gene name | Symbol | Accession No. (NCBI) | qPCR P (t test) |
|---|---|---|---|---|
| 211940_x_at | H3 histone, family 3A | H3F3A | BE869922 | 0.003 |
| 211943_x_at | Tumor protein, translationally-controlled 1 | TPT1 | AL565449 | 0.005 |
| 200748_s_at | Ferritin, heavy polypeptide 1 | FTH1 | NM_002032 | 0.008 |
| 210774_s_at | Nuclear receptor coactivator 4 | NCOA4 | AL162047 | 0.021 |
| 200059_s_at | Ras homolog gene family, member A | ARCR | BC001360 | 0.048 |
| 217733_s_at | Thymosin, beta 10 | THSMB | NM_021103 | 0.318 |
| 209685_s_at | Protein kinase C, beta 1 | PRKCB1 | M13975 | 0.615 |
| 208755_x_at | Ferritin, light polypeptide | FTL1 | BF312331 | 0.651 |
| 200086_s_at | Cytochrome c oxidase subunit IV isoform 1 | COX4I1 | AA854966 | 0.688 |
| 200971_s_at | Stress-associated endoplasmic reticulum protein 1; ribosome associated membrane protein 4 | SERP1 | NM_014445 | 0.868 |

Table 6 presents their quantitative alterations in serum from OSCC patients, determined by qPCR. The results confirmed that transcripts of H3F3A, TPT1, FTH1, NCOA4 and ARCR were significantly elevated in the saliva of OSCC patient (Wilcoxon Signed Rank test, P<0.05). We did not detect the statistically significant differences in the amount of the other five transcripts by qPCR.

Example 12: ROC and Sensitivity/Specificity Analysis

Statistical analysis of the data collected in outcome of the experiments reported on Examples 9 to 11 above demonstrates the specificity and sensitivity of these biomarkers for H NSCC, and their predictive value.

Receiver Operating Characteristic Curve Analysis and Prediction Models.

Utilizing the qPCR results, multivariate classification models were constructed to determine the best combination of the selected serum transcripts for cancer prediction. Firstly, using the binary outcome of the disease (OSCC) and non-disease (normal) as dependent variables, a logistic regression model was constructed [61]. Age, gender and smoking history are controlled in the data collection procedure.

Leave-one out cross validation was used to validate the logistic regression model. The cross validation strategy first removes one observation and then fits a logistic regression model from the remaining cases using all markers. Stepwise model selection is used for each of these models to remove variables that do not improve the model. Subsequently, the observing values for the case that was left out were used to compute a predicted class for that observation. The cross validation error rate is then the number of samples predicted incorrectly divided by the number of samples.

The Receiver operating characteristic (ROC) curve analysis was then computed for the best final logistic model (S-plus 6.0), using the fitted probabilities from the model as possible cut-points for computation of sensitivity and specificity. Area under the curve was computed via numerical integration of the ROC curve.

To demonstrate the utility of circulating mRNAs in serum for OSCC discrimination, two classification/prediction models were observed. Using the qPCR data, a logistic regression model was built compose of six serum transcripts previously examined, ARHA, FTH1, H3F3A, TPT1, COX4I1 and FTL1. Those six transcripts in combination provided the best prediction, which was then validated by the leaving-one-out validation. Out of 67 leaving-one-out trial, 54 (81%) of the best logistic models was found to the same model as the one from the whole data and the validation error rate was 31.3% (21/67).

Figure 9:
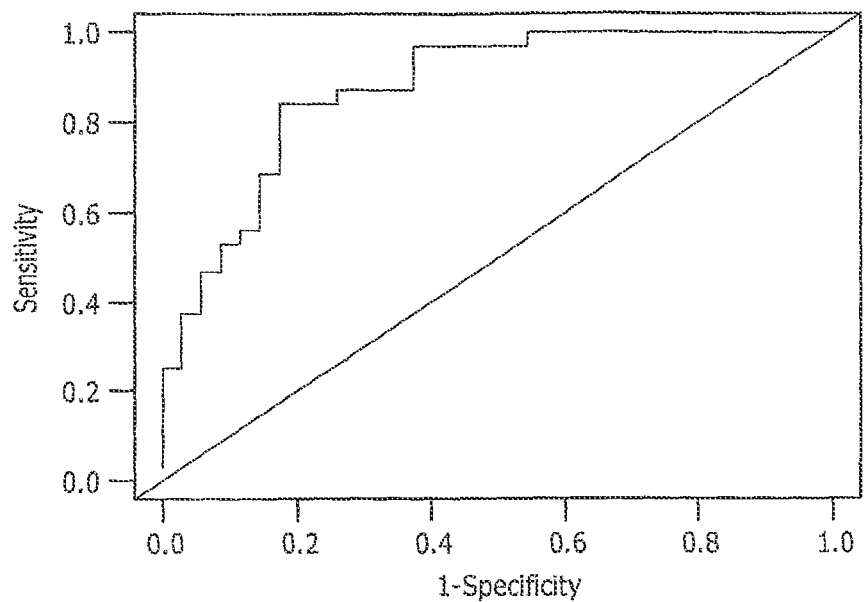
FIG. 9 shows a diagram reporting a ROC curve of the logistic regression model for the circulating mRNA in serum. On the x axis 1-specificity is reported. On y axis the sensitivity is reported.

Results are reported in FIG. 9, wherein the ROC curve computed for this logistic regression model is shown.

Using a cut-off probability of 44% a sensitivity of 84% and a specificity of 83% were obtained. The final model predicts correctly for 56 (83.5%) subjects out of 67 with 0.84 (27/32) sensitivity and 0.83 (29/35) specificity and it misclassifies 6 subjects for control and 5 for OSCC. The calculated area under the ROC curve was 0.88 for this logistic regression model.

Tree-Based Classification Model, Classification and Regression Tree (CART).

Secondly, another prediction model utilizing the qPCR results was built by a tree-based classification method. The classification and regression trees (CART), was constructed by S-plus 6.0 using the serum transcripts as predictors from qPCR result. CART fits the classification model by binary recursive partitioning, where each step involves searching for the predictor variable that results in the best split of the cancer versus the normal groups [62]. CART used the entropy function with splitting criteria determined by default settings for S-plus. By this approach, the parent group containing the entire samples (n=67) was subsequently divided into cancer groups and normal groups. Our initial tree was pruned to remove all splits that did not result in sub-branches with different classifications.

Figure 10:
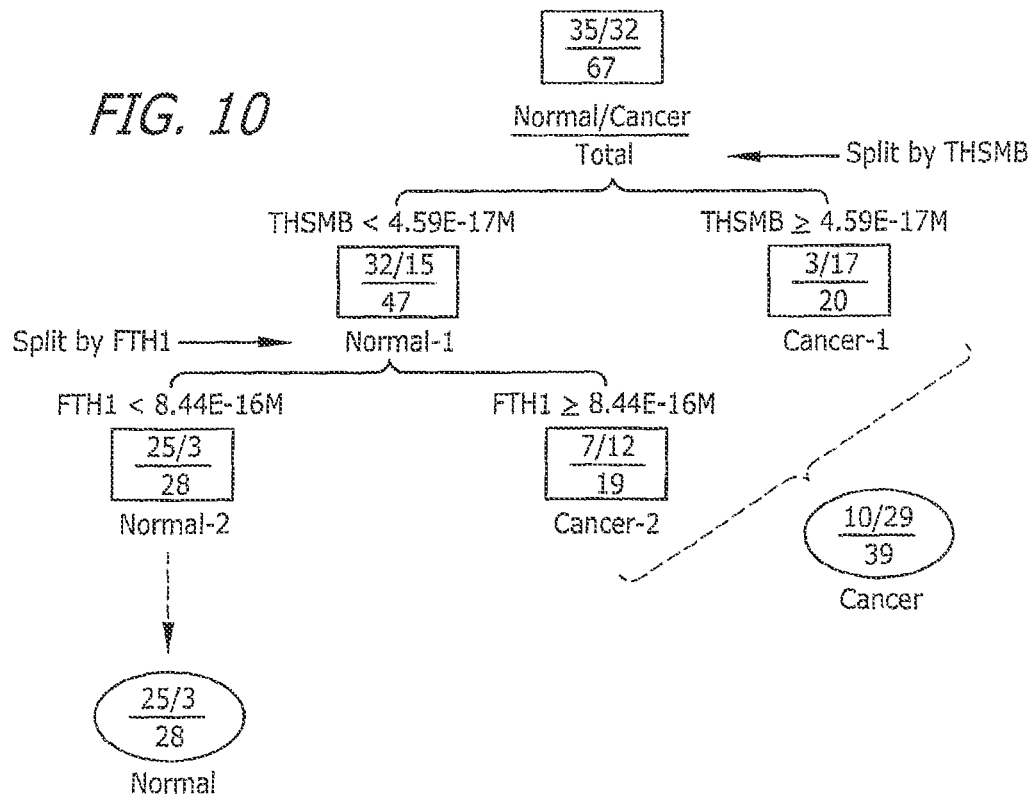
FIG. 10 shows a diagram reporting the classification and regression trees (CART) model assessing the serum mRNA predictors for OSCC

A second model, the "classification and regression trees (CART) model", was generated according to the diagram reported in FIG. 10.

Our fitted CART model used the serum mRNA concentrations of THSMB and FTH1 as predictor variables for OSCC. THSMB, chosen as the initial split, with a threshold of 4.59E-17 M, produced two child groups from the parent group containing the total 67 samples. 47 samples with the THSMB concentration <4.59E-17 M were assigned into "Normal-1", while 20 with THSMB concentration >4.59E-17 M were assigned into "Cancer-1". The "Normal-1" group was further partitioned by FTH1 with a threshold of 8.44E-16 M. The resulting subgroups, "Normal-2" contained 28 samples with FTH1 concentration <8.44E-16 M, and "Cancer-2" contained 19 samples with FTH1 concentration ≥8.44E-16 M. Consequently, the 67 serum samples involved in our study were classified into the "Normal" group and the "Cancer" group by CART analysis.

The "Normal" group was composed of the samples from "Normal-2" which included a total of 28 samples, 25 from normal subjects and 3 from cancer patients. Thus, by using the combination of THSMB and FTH1 for OSCC prediction, the overall specificity is 78% (25/35). The "Cancer" group was composed of the samples from "Cancer-1" and "Cancer-2". There are a total of 39 samples assigned in the final "Cancer" group, 29 from cancer patients and 10 from normal subjects. Therefore, by using the combination of these two serum mRNA for OSCC prediction, the overall sensitivity is 91% (29/32, in cancer group) and specificity is 78% (25/35, in normal group).

Example 13: RNA Isolation, Amplification and Gene Expression Profiling from Saliva of OSCC Patients Patient Selection.

OSCC patients were recruited from Medical Centers at University of California, Los Angeles (UCLA); University of Southern California (USC), Los Angeles, Calif.; and University of California San Francisco, San Francisco, Calif.

Thirty-two patients with documented primary T1 or T2 OSCC were included. All of the patients had recently received diagnoses of primary disease and had not received any prior treatment in the form of chemotherapy, radiotherapy, surgery, or alternative remedies.

An equal number of age- and sex-matched subjects with comparable smoking histories were selected as a control group. Among the two subject groups, there were no significant differences in terms of mean age: OSCC patients, 49.8±7.6 years; normal subjects, 49.1±5.9 years (Student's t test, $P>0.80$); gender ($P>0.90$); or smoking history ($P>0.75$). No subjects had a history of prior malignancy, immunodeficiency, autoimmune disorders, hepatitis, or HIV infection. All of the subjects signed the institutional review board-approved consent form agreeing to serve as saliva donors for the experiments.

Saliva Collection and RNA Isolation.

Unstimulated saliva samples were collected between 9 a.m. and 10 a.m. with previously established protocols [38]. Subjects were asked to refrain from eating, drinking, smoking, or oral hygiene procedures for at least 1 hour before the collection. Saliva samples were centrifuged at 2,600×g for 15 minutes at 4° C.

The supernatant was removed from the pellet and treated with RNase inhibitor (Superase-In, Ambion Inc., Austin, Tex.). RNA was isolated from 560 μl of saliva supernatant with QIAamp Viral RNA kit (Qiagen, Valencia, Calif.). Aliquots of isolated RNA were treated with RNase-free DNase (DNaseI-DNA-free, Ambion Inc.) according to the manufacturer's instructions. The quality of isolated RNA was examined by RT-PCR for three cellular maintenance gene transcripts: glyceraldehyde-3-phosphate dehydrogenase (GAPDH), actin-β(ACTB), and ribosomal protein S9 (RPS9). Only those samples exhibiting PCR products for all three mRNAs were used for subsequent analysis.

On average, 54.2±20.1 ng (n=64) of total RNA was obtained from 560 μl of saliva supernatant. There was no significant difference in total RNA quantity between the OSCC and matched controls (t test, P=0.29, n=64). RT-PCR results demonstrated that all of the saliva samples (n=64) contained transcripts from three genes (GAPDH, ACTB, and RPS9), which were used as quality controls for human salivary RNAs [55]. A consistent amplifying magnitude (658±47.2, n=5) could be obtained after two rounds of RNA amplification. On average, the yield of biotinylated cRNA was 39.3±6.0 μg (n=20). There were no significant differences or the cRNA quantity yielded between the OSCC and the controls (t test, P=0.31, n=20).

Example 14: Microarray Profiling of mRNA of Saliva from OSCC Patients

Saliva from 10 OSCC patients (7 male, 3 female; age, 52±9.0 years) and from 10 gender- and age-matched normal donors (age, 49±5.6 years) was used for a microarray study. Isolated RNA from saliva was subjected to linear amplification by RiboAmp RNA Amplification kit (Arcturus, Mountain View, Calif.). The RNA amplification efficiency was measured by using control RNA of known quantity (0.1 μg) running in parallel with the 20 samples in five independent runs.

Microarray Analysis.

Following previously reported protocols [55], the Human Genome U133A Array (HG U133A, Affymetrix, Santa Clara, Calif.) was applied for gene expression analysis. The arrays were scanned and the fluorescence intensity was measured by Microarray Suit 5.0 software (Affymetrix, Santa Clara, Calif.); the arrays were then imported into DNA-Chip Analyzer software (http: www.dchp.org) for normalization and model-based analysis [60]. S-plus 6.0 (Insightful, Seattle, Wash.) was used to carry out all statistical tests.

Three criteria were used to determine differentially expressed gene transcripts. First, probe sets on the array that were assigned as "absent" call in all samples were excluded. Second, a two-tailed Student's t test was used for comparison of average gene expression signal intensity between the OSCCs (n=10) and controls (n=10). The critical level of 0.05 was defined for statistical significance. Third, fold ratios were calculated for those gene transcripts that showed statistically significant difference ($P<0.05$). Only those gene transcripts that exhibited at least 2-fold change were included for further analysis.

The HG U133A microarrays were used to identify the difference in salivary RNA profiles between cancer patients and matched normal subjects. Among the 10,316 transcripts included by the previously described criteria, we identified 1,679 transcripts with P value less than 0.05. Among these transcripts, 836 were up-regulated and 843 were down-regulated in the OSCC group. These transcripts observed were unlikely to be attributable to chance alone (2 test, $P<0.0001$), considering the false positives with $P<0.05$. Using a predefined criteria of a change in regulation >3-fold in all 10 OSCC saliva specimens and a cutoff of P value <0.01, 17 mRNA, were identified showing significant up-regulation in OSCC saliva. 17 transcripts showed a change in regulation >3-fold in all 10 OSCC saliva specimens, and a more stringent cutoff of P value <0.01. It should be noted that these 17 salivary mRNA are all up-regulated in OSCC saliva, whereas there are no mRNAs found down-regulated with the same filtering criteria. The biological functions of these genes and their products are presented in Table 7 showing Salivary mRNA up-regulated (>3-fold, $P<0.01$) in OSCC identified by microarray

TABLE 7

| Gene symbol | Gene name | GenBank accession No. | Locus | Gene Functions |
| --- | --- | --- | --- | --- |
| B2M | β-2-microglobulin | NM_04048 | 15q21-q22.2 | Antiapoptosis; antigen presentation |
| DUSP1 | Dual specificity phosphatase 1 | NM_04417 | 5q34 | Protein modification; signal transduction oxidative stress; |

TABLE 7-continued

| Gene symbol | Gene name | GenBank accession No. | Locus | Gene Functions |
|---|---|---|---|---|
| FTH1 | Ferritin, heavy polypeptide 1 | NM_02032 | 11q13 | Iron ion transport; cell proliferation |
| GOS2 | Putative lymphocyte GO-G1 switch gene | NM_015714 | 1q32.2-q41 | Cell growth and/or maintenance; regulation of cell cycle |
| GADD45B | Growth arrest and DNA-damage-inducible β | NM_015675 | 19p13.3 | Kinase cascade; apoptosis |
| H3F3A | H3 histone, family 3A | BE869922 | 1q41 | DNA binding activity |
| HSPC016 | Hypothetical protein HSPC016 | BG167522 | 3p21.31 | Unknown |
| IER3 | Immediate early response 3 | NM_003897 | 6p21.3 | Embryogenesis; morphogenesis; apoptosis; cell growth and maintenance |
| IL1B | Interleukin 1β | M15330 | 2q14 | Signal transduction; proliferation; inflammation apoptosis |
| IL8 | Interleukin 8 | NM_000584 | 4q13-q21 | Angiogenesis; replication; calcium-mediated signaling pathway; cell adhesion; chemotaxis cell cycle arrest; immune response |
| MAP2K3 | Mitogen-activated protein kinase kinase 3 | AA780381 | 17q11.2 | Signal transduction; protein modification |
| OAZ1 | Ornithine decarboxylase antizyme 1 | D87914 | 19p13.3 | Polyamine biosynthesis |
| PRG1 | Proteoglycan 1, secretory granule | NM_002727 | 10q22.1 | Proteoglycan |
| RGS2 | Regulator of G-protein signaling 2, 24 kda | NM_002923 | 1q31 | Oncogenesis; G-protein signal transduction |
| S100P | S100 calcium binding protein P | NM_005980 | 4p16 | Protein binding; calcium ion binding |
| SAT | Spermidine/spermine N1-acetyltransferase | NM_002970 | Xp22.1 | Enzyme, transferase activity |
| EST | highly similar ferritin light chain | BG537190 |  | Iron ion homeostasis, ferritin complex |

The human Genome U133A microarrays were used to identify the difference in RNA expression patterns in saliva from 10 cancer patients and 10 matched normal subjects. Using a criteria of a change in regulation >3-fold in all 10 OSCC saliva specimens and a cutoff of P value <0.01, we identified 17 mRNA, showing significant up-regulation in OSCC saliva.

Example 15: Q-PCR Validation and Quantitation Analysis of Microarray Profiling from Cell-Free Saliva of OSCC Patients Quantitative polymerase chain reaction (qPCR) was performed to validate a subset of differently expressed transcripts identified by the microarray analysis of Example 14. Quantitative Polymerase Chain Reaction Validation.

cDNA from the original and unamplified salivary RNA. was synthesized Using MuLV reverse transcriptase (Applied Biosystems, Foster City, Calif.) and random hexamers as primer (Applied Biosystems). The qPCR reactions were performed in an iCycler PCR system with IQ SYBR Green Supermix (Bio-Rad, Hercules, Calif.). Primer sets were designed by using PRIMER3 software (http://www.genome.wi.mit.edu).

All of the reactions were performed in triplicate with customized conditions for specific products. The initial amount of cDNA/RNA of a particular template was extrapolated from the standard curve as described previously [32]. This validation completed by testing all of the samples (n=64) including those 20 previously used for microarray study. Wilcoxon Signed-Rank test was used for statistical analysis.

Quantitative PCR was performed to validate the microarray findings on an enlarged sample size including saliva from 32 OSCC patients and 32 matched controls. Nine candidates of salivary mRNA biomarkers: DUSP1, GADD45B, H3F3A, IL1B, IL8, OAZ1, RGS2, S100P, and SAT were selected based on their reported cancer association reported in Table 7. Table 8 presents the quantitative alterations of the above nine candidates in saliva from OSCC patients, determined by qPCR.

TABLE 8

| Gene symbol | Primer sequence (5' to 3') | Validated * | P value | Mean fold increase |
|---|---|---|---|---|
| DUSP1 | F: SEQ ID NO: 35<br>R: SEQ ID NO: 36 | Yes | 0.039 | 2.60 |
| H3F3A | F: SEQ ID NO: 37<br>R: SEQ ID NO: 38 | Yes | 0.011 | 5.61 |
| IL1B | F: SEQ ID NO: 39<br>R: SEQ ID NO: 40 | Yes | 0.005 | 5.48 |
| IL8 | F: SEQ ID NO: 41<br>R: SEQ ID NO: 42 | Yes | 0.000 | 24.3 |
| OAZ1 | F: SEQ ID NO: 43<br>R: SEQ ID NO: 44 | Yes | 0.009 | 2.82 |
| S100P | F: SEQ ID NO: 45<br>R: SEQ ID NO: 46 | Yes | 0.003 | 4.88 |

TABLE 8-continued

| Gene symbol | Primer sequence (5' to 3') | Validated * | P value | Mean fold increase |
|---|---|---|---|---|
| SAT | F: SEQ ID NO: 47<br>R: SEQ ID NO: 48 | Yes | 0.005 | 2.98 |
| GADD45B | F: SEQ ID NO: 49<br>R: SEQ ID NO: 50 | No | 0.116 | |
| RGS2 | F: SEQ ID NO: 51<br>R: SEQ ID NO: 52 | No | 0.149 | |

Seven of the nine potential candidate were validated by qPCR ($P < 0.05$).
* Wilcoxon's Signed Rank test: if $P < 0.05$, validated (Yes); if P .gtoreq. 0.05, not validated (No)

The results confirmed that transcripts of 7 of the 9 candidate mRNA (78%), DUSP1, H3F3A, IL1B, IL8, OAZ1, S100P, and SAT, were significantly elevated in the saliva of OSCC patient (Wilcoxon Signed-Rank test, $P<0.05$). We did not detect the statistically significant differences in the amount of RGS2 ($P=0.149$) and GADD45B ($P=0.116$) by qPCR. The validated seven genes could be classified in three ranks by the magnitude of increase: high up-regulated mRNA including IL8 (24.3-fold); moderate up-regulated mRNAs including H3F3A (5.61 fold), IL1B (5.48), and low up-regulated mRNAs including DUSP1 (2.60-fold), OAZ1 (2.82-fold), and SAT (2.98-fold).

Example 16: ROC and Sensitivity/Specificity Analysis

Using the qPCR results, Receiver Operating Characteristic (ROC) curve analyses was performed [82] by S-plus 6.0 to evaluate the predictive power of each of the biomarkers identified in the Example 15.
Receiver Operating Characteristic Curve Analysis and Prediction Models.

The optimal cutpoint was determined for each biomarker by searching for those that yielded the maximum corresponding sensitivity and specificity. ROC curves were then plotted on the basis of the set of optimal sensitivity and specificity values. Area under the curve was computed via numerical integration of the ROC curves. The biomarker that has the largest area under the ROC curve was identified as having the strongest predictive power for detecting OSCC.

Next, multivariate classification models were constructed to determine the best combination of salivary markers for cancer prediction. Firstly, using the binary outcome of the disease (OSCC) and nondisease (normal) as dependent variables, we constructed a logistic regression model controlling for patient age, gender, and smoking history. The backward stepwise regression [61] was used to find the best final model.

Leave-one-out cross-validation was used to validate the logistic regression model. The cross-validation strategy first removes one observation and then fits a logistic regression model from the remaining cases with all of the markers. Stepwise model selection is used for each of these models to remove variables that do not improve the model. Subsequently, the marker values were used for the case that was left out to compute a predicted class for that observation. The cross-validation error rate is then the number of samples predicted incorrectly divided by the number of samples.

Figure 11:
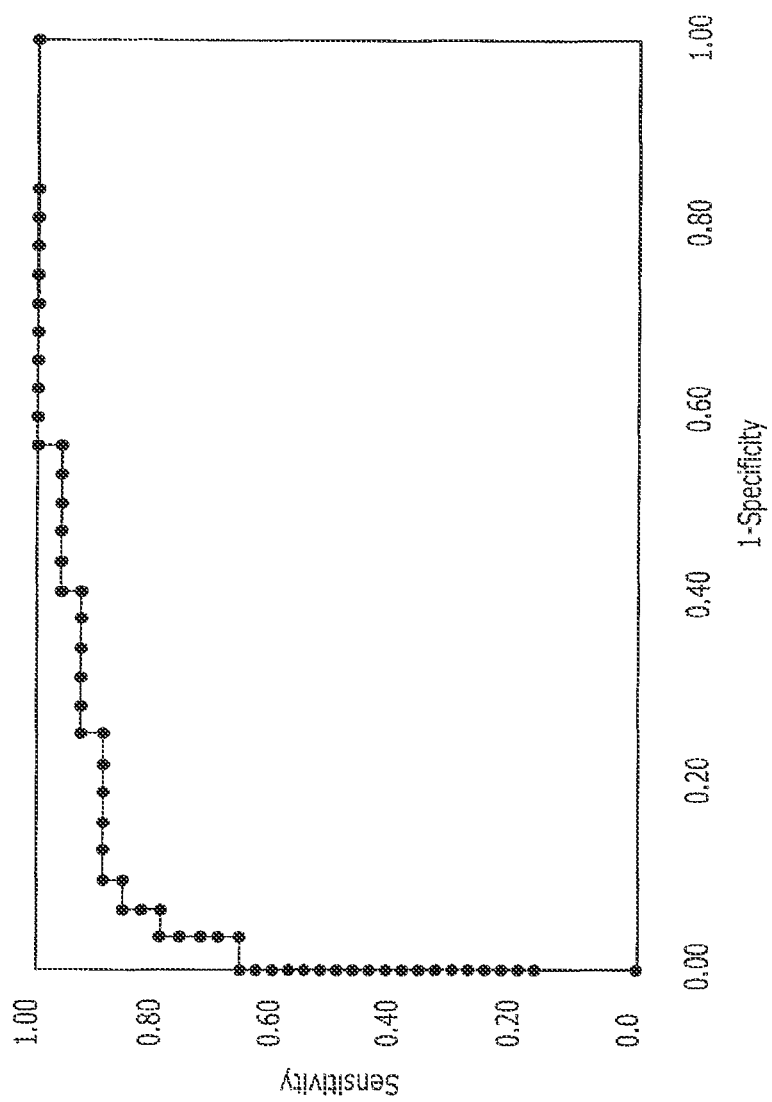
FIG. 11 shows a diagram reporting a ROC curve of the logistic regression model for the predictive power of combined salivary mRNA biomarkers. On the x axis 1-specificity is reported. On y axis the sensitivity is reported.

The ROC curve, illustrated in FIG. 11, was then computed for the logistic model by a similar procedure, with the fitted probabilities from the model as possible cutpoints for computation of sensitivity and specificity.

The detailed statistics of the area under the receiver operator characteristics (ROC) curves, the threshold values, and the corresponding sensitivities and specificities for each of the seven potential salivary mRNA biomarkers for OSCC are listed in Table 9 showing the ROC curve analysis of OSCC-associated salivary mRNA biomarkers

TABLE 9

| Biomarker | Area under ROC curve | Threshold/cutoff (M) | Sensitivity (%) | Specificity (%) |
|---|---|---|---|---|
| DUSP1 | 0.65 | 8.35E–17 | 59 | 75 |
| H3F3A | 0.68 | 1.58E–15 | 53 | 81 |
| IL1B | 0.70 | 4.34E–16 | 63 | 72 |
| IL8 | 0.85 | 3.19E–18 | 88 | 81 |
| OAZ1 | 0.69 | 7.42E–17 | 100 | 38 |
| S100P | 0.71 | 2.11E–15 | 72 | 63 |
| SAT | 0.70 | 1.56E–15 | 81 | 56 |

Utilizing the qPCR results, we conducted ROC curve analyses to evaluate the predictive power of each of the biomarkers. The optimal cutpoint was determined yielding the maximum corresponding sensitivity and specificity. The biomarker that has the largest area under the ROC curve was identified as having the strongest predictive power for detecting OSCC.

The data showed IL8 mRNA performed the best among the seven potential biomarkers for predicting the presence of OSCC. The calculated area under the ROC curve for IL8 was 0.85. With a threshold value of 3.19E-18 mol/L, IL8 mRNA in saliva yields a sensitivity of 88% and a specificity of 81% to distinguish OSCC from the normal.

To demonstrate the utility of salivary mRNAs for disease discrimination, two classification/prediction models were examined. A logistic regression model was built based on the four of the seven validated biomarkers, IL1B, OAZ1, SAT, and IL8, which in combination provided the best prediction (Table 10). Table 10 shows salivary for OSCC selected by 1 ogistic regression model

TABLE 10

| Biomarker | Coefficient value | SE | P value |
|---|---|---|---|
| Intercept | −4.79 | 1.51 | 0.001 |
| IL1B | 5.10E+19 | 2.68E+19 | 0.062 |
| OAZ1 | 2.18E+20 | 1.08E+20 | 0.048 |
| SAT | 2.63E+19 | 1.10E+19 | 0.020 |
| IL8 | 1.36E+17 | 4.75E+16 | 0.006 |

The logistic regression model was built based on the four of seven validated biomarkers (IL1B, OAZ1, SAT, and IL8) that, in combination, provided the best prediction. The coefficient values are positive for these four markers, indicating that the synchronized increase in their concentrations in saliva increased the probability that the sample was obtained from an OSCC subject.

The coefficient values are positive for these four markers, indicating that the synchronized rise in their concentrations in saliva increased the probability that the sample was obtained from an OSCC subject. The leave-one-out cross-validation error rate based on logistic regression models was 19% (12 of 64). All but one (of the 64) of the models generated in the leave-one-out analysis used the same set of four markers found to be significant in the full data model specified in Table 10.

The ROC curve was computed for the logistic regression model. Using a cutoff probability of 50%, we obtained a sensitivity of 91% and a specificity of 91%. The calculated area under the ROC curve was 0.95 for the logistic regression model (FIG. 11).

Tree-Based Classification Model, Classification and Regression Tree (CART).

A second model, a tree-based classification model, classification and regression tree (CART) model," was generated. The CART model was constructed by S-plus 6.0 with the validated mRNA biomarkers as predictors. CART fits the classification model by binary recursive partitioning, in which each step involves searching for the predictor variable that results in the best split of the cancer versus the normal groups [62]. CART used the entropy function with splitting criteria determined by default settings for S-plus. By this approach, the parent group containing the entire samples (n=64) was subsequently divided into cancer groups and normal groups. Our initial tree was pruned to remove all splits that did not result in sub-branches with different classifications.

Figure 12:
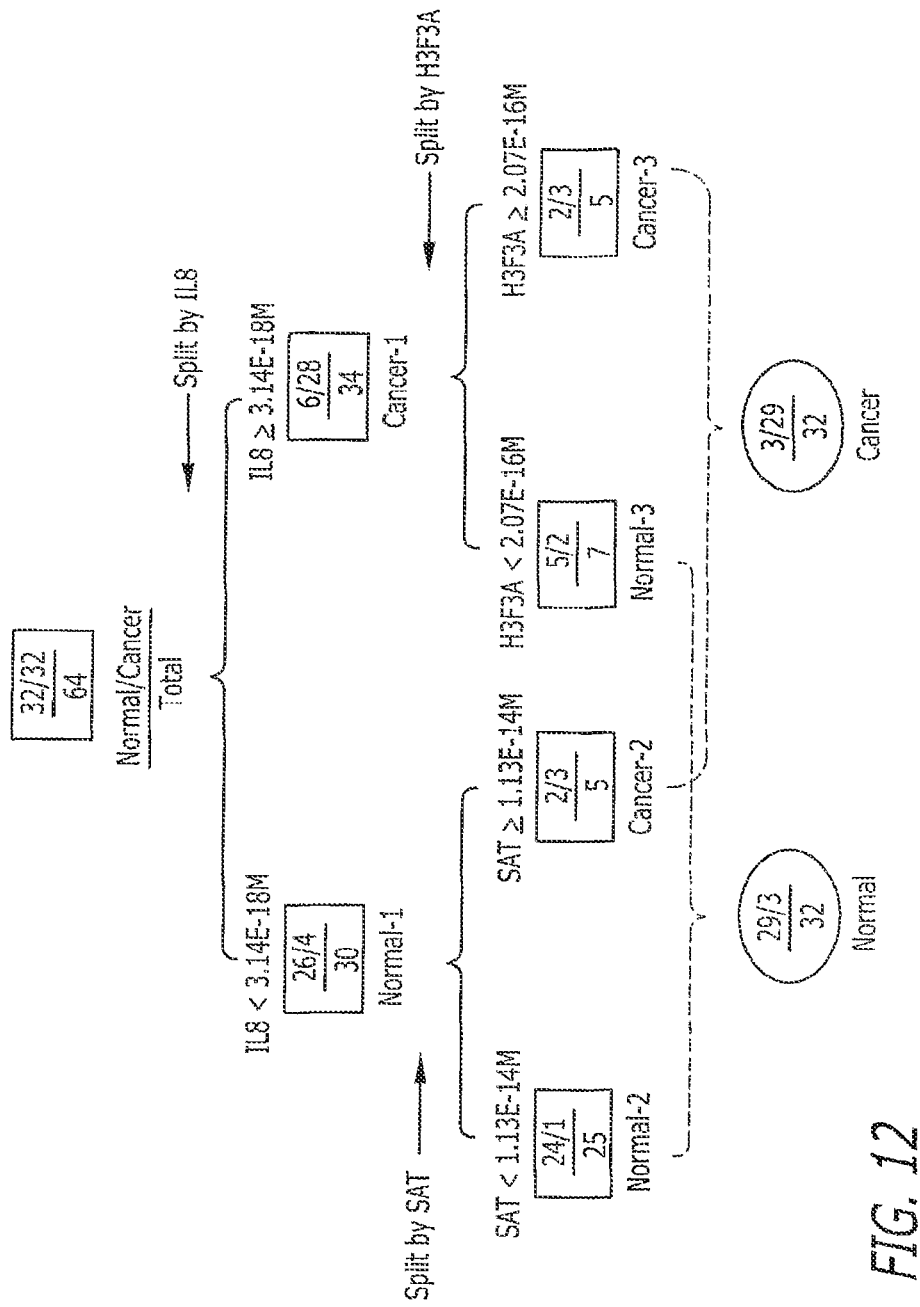
FIG. 12 shows a diagram reporting the classification and regression trees (CART) model assessing the salivary mRNA predictors for OSCC.

Results are shown in the diagram of FIG. 12. Our fitted CART model used the salivary mRNA concentrations of IL8, H3F3A, and SAT as predictor variables for OSCC. IL8, chosen as the initial split, with a threshold of 3.14E_18 mol/L, produced two child groups from the parent group containing the total 64 samples. 30 samples with the IL8 concentration <3.14E-18 mol/L were assigned into "Normal-1," whereas 34 with IL8 concentration ≥3.14E-18 were assigned into "Cancer-1". The "Normal-1" group was further partitioned by SAT with a threshold of 1.13E-14 mol/L.

The resulting subgroups, "Normal-2" contained 25 samples with SAT concentration <1.13E-14 mol/L, and "Cancer-2" contained 5 samples with SAT concentration. ≥1.13E-14 mol/L. Similarly, the "Cancer-1" group was further partitioned by H3F3A with a threshold of 2.07E-16 mol/L. The resulting subgroups, "Cancer-3" contained 27 samples with H3F3A concentration ≥2.07E-16 mol/L, and "Normal-3" group contained 7 samples with H3F3A concentration <2.07E-16 mol/L.

Consequently, the 64 saliva samples involved in our study were classified into the "Cancer" group and the "Normal" group by CART analysis. The "Normal" group was composed of the samples from "Normal-2" and those from "Normal-3". There are a total of 32 samples assigned in the "Normal" group, 29 from normal subjects and 3 from cancer patients.

Thus, by using the combination of IL8, SAT, and H3F3A for OSCC prediction, the overall sensitivity is 90.6% (29 of 32). The "Cancer" group was composed of the samples from "Cancer-2 and Cancer-3". There are a total of 32 samples assigned in the final "Cancer" group, 29 from cancer patients and 3 from normal subjects. Therefore, by using the combination of these three salivary mRNA biomarkers for OSCC prediction, the overall specificity is 90.6% (29 of 32).

In summary the present disclosure refers to a method to detect a biomarker in saliva wherein the biomarker is an extracellular mRNA, comprises detecting the extracellular mRNA in the cell-free saliva; transcriptome analysis of saliva comprises detecting a transcriptome pattern in the cell-free saliva; a method to detect genetic alterations in an organ or in a gene in the organ by analyzing saliva, comprises detecting a transcriptome pattern and/or the mRNA profiling of the gene in cell-free saliva; a method to diagnose an oral or systemic pathology disease or disorder in a subject, comprises: detecting profile of a biomarker associated with the pathology disease or disorder, in particular mRNA and/or protein, in cell-free saliva and/or serum; kits comprising identifier for at least one biomarker for performing at least one of the methods; and use of salivary biomarker salivary and/or serum mRNAs as biomarkers for oral and/or systemic pathology, disease or disorder.

The disclosures of each and every publication and reference cited herein are hereby incorporated herein by reference in their entirety.

The present disclosure has been explained with reference to specific embodiments. Other embodiments will be apparent to those of ordinary skill in the art in view of the foregoing description. The scope of protection of the present disclosure is defined by the appended claims.

REFERENCES

[1] Parkin M, Pisani P, Ferlay J. Estimates of the worldwide incidence of 25 major cancers in 1990. Int J. Cancer. 1999; 80:827-841.

[2] Goeptert H. squamous cell carcinoma or the head and neck, past progress and future promise. CA Cancer J Clin. 1998; 48:195-198.

[3] Sidransky D. Emerging molecular markers of cancer. Nat Reviews. 2002; 3:210-219.

[4] Alevizos I, Mahadevappa M, Zhang X, et al. Oral cancer in vivo gene expression profiling assisted by laser-capture microdissection and microarray analysis. Oncogene. 2001; 20:6196-6204.

[5] Chen Z, Malhotra P S, Thomas G R, et al. Expression of proinflammatory and proangiogenic cytokines in patients with head and neck cancer. Clin Cancer Res. 1999; 5:1369-1379.

[6] Sidransky D. Nucleic acid-based methods for the detection of cancer. Science. 1997; 278: 1054-1058.

[7] Navazesh M, Christensen C A. A comparison of whole mouth resting and stimulated salivary measurements. J. Dent. Res. 1982; 61:1158-1162.

[8] Hanley J A, McNeil B J. The meaning and use of the area under a receiver operating characteristic (ROC) curve. Radiology. 1982; 143:29-36.

[9] Hanley J A, McNeil B J. A method of comparing the areas under receiver operating characteristic curves derived from the same cases. Radiology. 1983; 148:839-843.

[10] Liu H H, Wu T T. Estimating the area under a receiver operating characteristic (ROC) curve for repeated measures design. Journal of Statistical Software. 2003; 8:1-18.

[11] Norton J A, Peacock I L, Morrison S D. Cancer cachexia. Crit Rev Oncol Hematol. 1987; 7:289-327.

[12] Smith D R, Polverini P J, Kunkel S L, et al. Inhibition or interleukin 8 attenuates angiogenesis in bronchogenic carcinoma. J Exp Med. 1994; 179:1409-1415.

[13] Dong G, Loukinova E, Smith C W, Chen Z, and Van Waes C. Genes differentially expressed with malignant transformation and metastatic tumor progression of murine squamous cell carcinoma. J Cell Biochem Suppl. 1997; 28/29:90-100.

[14] Pak A S, Wright M A, Matthews J P, et al. Mechanisms of immune suppression in patients with head and neck cancer: presence of CD34+ cells which suppress immune functions within cancers that secrete granulocyte-macrophage colony-stimulating factor. Clin Cancer Res. 1995; 1:95-103.

[15] Ueda T, Shimada E, Urakawa T. Serum levels of cytokines in patients with colorectal cancer: possible involvement of interleukin-6 and interleukin-8 in hematogenous metastasis. J. Gastroenterol. 1994; 29:423-429.

[16] Oka M, Yamamoto K, Takahashi M, et al. Relationship between serum levels of interleukin 6, various disease parameters, and malnutrition in patients with esophageal squamous cell. carcinoma. Cancer Res. 1996; 56:2776-2780.

[17] Wang P L, Ohura K, Fujii T, Oido-Mori M, Kowashi Y, Kikuchi M, Suetsugu Y, Tanaka J. DNA microarray analysis of human gingival fibroblasts from healthy and inflammatory gingival tissues. Biochem Biophys Res Commun. 2003; 305:970-973.

[18] Giannopoulou C, Kamma J J, Mombelli A. Effect of inflammation, smoking and stress on gingival crevicular fluid cytokine level. J Clin Periodontol. 2003; 30:145-153.

[19] Sullivan Pepe M, Etzioni R, Feng Z, et al. Phases of biomarker development for early detection of cancer. J National Can Inst. 2001; 93:1054-1061.

[20] van Houten V M, Tabor M P, van den Berker M W, et al. Molecular assays for the diagnosis of minimal residual head-and-neck cancer: methods, reliability, pitfalls, and solutions. Clin Cancer Res. 2000; 6:3803-3816.

[21] Thompson M L, Zucchini W. On the statistical analysis of ROC curves. Stat Med. 1989; 8:1277-1290.

[22] Hoffman H T, Karnell L H, Funk G F, Robinson R A, Menck H R. The national cancer data base report on cancer of the head and neck. Arch Otolaryngol Head Neck Surg. 1998; 124:951-962.

[23] Khuri F R, Shin D M, Glisson B S, Lippman S M, Hong W K. Treatment of patients with recurrent or metastatic squamous cell carcinoma of the head and neck: current status and future directions. Semin Oncol. 2000; 27:25-33.

[24] Spafford M F, Koch W M, Reed A L, et al. Detection of head and neck squamous cell carcinoma among exfoliated oral cells by microsatellite analysis. Clin Cancer Res. 2001; 7:607-612.

[25] Bradford C R. Genetic markers of head and neck cancer: identifying new molecular targets. Arch Otolaryngol Head Neck Surg. 2003; 129:366-367.

[26] Koch W M. Genetic markers in the clinical care of head and neck cancer: slow in coming. Arch Otolaryngol Head Neck Surg. 2003; 129:367-368.

[27] Affymetrix, (2001). Affymetrix Technical Note: New Statistical Algorithms for Monitoring Gene Expression on GeneChip® Probe Arrays. Santa Clara, C A: Affymetrix.

[28] Anker P, Mulcahy H, Chen X Q, Stroun M (1999). Detection of circulating tumor DNA in the blood (plasma/serum) of cancer patients. Cancer Metastasis Rev 18(1): 65-73.

[29] Anker P, Mulcahy H, Stroun M (2003). Circulating nucleic acids in plasma and serum as a noninvasive investigation for cancer: time for large-scale clinical studies? Int J Cancer 103(2): 149-152.

[30] Bonassi 5, Neri M, Puntoni R (2001). Validation of biomarkers as early predictors of disease. Mutat Res 480-481: 349-358.

[30] El-Naggar A K, Mao L, Staerkel G, Coombes M M, Tucker S L, Luna M A, et al (2001). Genetic heterogeneity in saliva from patients with oral squamous carcinomas: implications in molecular diagnosis and screening. J Mol Diagn 3(4): 164-170.

[31] Fleischhacker M, Beinert T, Ermitsch M, Seferi D, Possinger K, Engelmann C, et al (2001). Detection of amplifiable messenger RNA in the serum of patients with lung cancer. Ann NY Acad Sci 945: i79-188.

[32] Ginzinger D (2002). Gene quantification using real-time quantitative PCR: an emerging technology hits the mainstream. Exp Hemato 30: 503-512.

[33] Kelly J J, Chernov B K, Tovstanovsky I, Mirzabekov A D, Bavykin S G (2002). Radical-generating coordination complexes as tools for rapid and effective fragmentation and fluorescent labeling of nucleic acids for microchip hybridization. Anal Biochem 311(2): 103-118.

[34] Kopreski M S, Benko F A, Kwak L W, Gocke C D (1999). Detection of tumor messenger RNA in the serum of patients with malignant melanoma. Clin Cancer Res 5:1961-1965.

[35] Lawrence H P (2002). Salivary markers of systemic disease: noninvasive diagnosis of disease and monitoring of general health. J Can Dent Assoc 68(3):170-174.

[36] Liao P H, Chang Y C, Huang M F, Tai K W, Chou M Y (2000). Mutation of p53 gene codon 63 in saliva as a molecular marker for oral squamous cell carcinomas. Oral Oncol 36(3):272-276.

[37] Mercer D K, Scott K P, Melville C M, Glover L A, Flint H J (2001). Transformation of an oral bacterium via chromosomal integration of free DNA in the presence of human saliva. FEMS Microbiol Lett 200(2): 163-167.

[38] Navazesn M (1993). Methods for collecting saliva. Ann N Y Acad Sci 694:72-77.

[39] Ohyama H, Zhang X, Kohno Y, Alevizos I, Posner M, Wong D T, et al (2000). Laser capture microdissection-generated target sample for high-density oligonucleotide array hybridization. Biotechniques 29(3): 530-536.

[40] Pusch W, Flocco M T. Leung S M, Thiele H, Kostrzewa M (2003). Mass spectrometry-based clinical proteomics. Pharmacogenomics 4(4):463-476.

[41] Rehak N N, Cecco S A, Csako G (2000). Biochemical composition and electrolyte balance of "unstimulated" whole human saliva. Clin Chem Lab Med 38(4):33 5-343.

[42] Rieger-Christ K M, Mourtzinos A, Lee P J, Zagha R M, Cain J, Silverman M, et al (2003). Identification of fibroblast growth factor receptor 3 mutations in urine sediment DNA samples complements cytology in bladder tumor detection. Cancer 98(4):737-744.

[43] Sakki T, Knuuttila M (1996). Controlled study of the association of smoking with lactobacilli, mutans streptococci and yeasts in saliva. Eur J Oral Sci 104(5-6):619-622.

[44] Horer, O. L. and G. Palicari, RNase activity in the capillary blood of children. Virologie, 1986. 37(2): p. 111-114

[45] Sidransky D (2002). Emerging molecular markers of cancer. Nat Reviews 3:210-219.

[46] Stamey F R, DeLeon-Carnes M, Patel M M, Pellett P E, Dollard S C (2003). Comparison of a microtiter plate system to Southern blot for detection of human herpesvirus 8 DNA amplified from blood and saliva. J Virol Methods 108(2):189-193.

[47] Streckfus C F, Bigler L R (2002). Saliva as a diagnostic fluid. Oral Dis 8(2):69-76.

[48] Venter J C, Adams M D, Myers E W, Li P W, Mural R J, Sutton G G et al (2001). The sequence of the human genome (published erratum appears in Science 292(5 523): 1838). Science 291(5507): 1304-1351.

[49] Wong U, Lueth M, Li X N, Lau C C, Vogel H (2003). Detection of mitochondrial DNA mutations in the tumor and cerebrospinal fluid of medulloblastoma patients. Cancer Res 63(14). 3866-3871.

[50] Xiang C C, Chen M, Ma L, Phan Q N, Inman J M, Kozhich O A, et al (2003). A new strategy to amplify

[51] Lipshutz, R. J., et al., High density synthetic oligonucleotide arrays. Nat Genet, 1999. 21(1 Suppl): p. 20-4.
[52] Lipshutz, R. J., Applications of high-density oligonucleotide arrays. Novartis Found Symp, 2000. 229: p. 84-90; discussion 90-3.
[53] Barker, P. E., Cancer biomarker validation: standards and process: roles for the National Institute of Standards and Technology (NIST). Ann N Y Acad Sci, 2003. 983: p. 142-50.
[54] Juusola, J. and J. Ballantyne, Messenger RNA profiling: a prototype method to supplant conventional methods for body fluid identification. Forensic Sci Int, 2003. 135(2): p. 85-96.
[55] Li, Y., et al., RNA profiling of cell-free saliva using microarray technology. J Dent Res, 2004. 83(3): p. 199-203.
[56] Kopreski, M. S., F. A. Benko, and C. D. Gocke, Circulating RNA as a tumor marker: detection of 5T4 mRNA in breast and lung cancer patient serum. Ann N Y Acad Sci, 2001. 945: p. 172-178.
[57] Bunn, P. J., Jr., Early detection of lung cancer using serum RNA or DNA markers: ready for "prime time" or for validation? J Clin Oncol, 2003. 21(21): p. 3891-3893.
[58] Wong, S. C., et al., Quantification or plasma beta-carenin mRNA in colorectal cancer and adenoma patients. Clin Cancer Res, 2004. 10(5): p. 1613-1617.
[59] Fugazzola, L., et al., Highly sensitive serum thyroglobulin and circulating thyroglobulin mRNA evaluations in the management of patients with differentiated thyroid cancer in apparent remission. J Clin Endocrinol Metab, 2002. 87(7): p. 3201-8.
[60] Li, C. and W. H. Wong, Model-based analysis of oligonucleotide arrays: expression index computation and outlier detection. Proc Natl Acad Sci USA, 2001. 98(1): p. 31-36.
[61] Renger, R. and L. M. Meadows, Use of stepwise regression in medical education research. Acad Med, 1994. 69(9): p. 738.
[62] Lemon, S. C., et al., Classification and regression tree analysis in public health: methodological review and comparison with logistic regression. Ann Behav Med, 2003. 26(3): p. 172-181.
[63] Cancer facts and FIGS. 2004. Atlanta: American Cancer Society, 2004.
[64] Wildt, J., T. Bundgaard, and S. M. Bentzen, Delay in the diagnosis of oral squamous cell carcinoma. Clin Otolaryngol, 1995. 20(1): p. 21-25
[65] Fong, K. M., et al., Molecular genetic basis for early cancer detection and cancer susceptibility., in Molecular Pathology of Early Cancer, S. S. H D and G. A F, Editors. 1999, IOS Press. p. 13-26.
[66] Epstein, J. B., L. Zhang, and M. Rosin, Advances in the diagnosis of oral premalignant and malignant lesions. J Can Dent Assoc, 2002. 68(10): p. 617-621.
[67] Mao, L., W. K. Hong, and V. A. Papadimitrakopoulou, Focus on head and neck cancer. Cancer Cell, 2004. 5(4): p. 311-316
[68] Li, Y., et al., Salivary transcriptome diagnostics for oral cancer detection. Clin Cancer Res, 2004. 10(24): p. 8442-8450.
[69] Ng, E. K., et al., Presence of filterable and nonfilterable mRNA in the plasma of cancer patients and healthy individuals. Clin Chem, 2002. 48(8): p. 1212-1217
[70] Jung, K., et al., Increased cell-free DNA in plasma of patients with metastatic spread in prostate cancer. Cancer Lett, 2004. 205(2): p. 173-180
[71] Wang, B. G., et al., Increased plasma DNA integrity in cancer patients. Cancer Res, 2003. 63(14): p. 3966-3968.
[72] Lo, Y. M., et al., Quantitative analysis of cell-free Epstein-Barr virus DNA in plasma of patients with nasopharyngeal carcinoma. Cancer Res, 1999. 59(6): p. 1188-1191
[73] Chen, X. Q., et al., Telomerase RNA as a detection marker in the serum of breast cancer patients. Clin Cancer Res, 2000. 6(10): p. 3823-3826.
[74] Silva, J. M., et al., Detection of epithelial messenger RNA in the plasma of breast cancer patients is associated with poor prognosis tumor characteristics. Clin Cancer Res, 2001. 7(9): p. 2821-2825.
[75] Dasi, F., et al., Real-time quantification in plasma of human telomerase reverse transcriptase (hTERT) mRNA: a simple blood test to monitor disease in cancer patients. Lab Invest, 2001. 81(5): p. 767-769
[76] Bernard, P. S. and C. T. Wittwer, Real-time PCR technology for cancer diagnostics. Clin Chem, 2002. 48(8): p. 1178-1185.
[77] Jahr, S., et al., DNA fragments in the blood plasma of cancer patients: quantitations and evidence for their origin from apoptotic and necrotic cells. Cancer Res, 2001. 61(4): p. 1659-1665
[78] Stroun, M., et al., Neoplastic characteristics of the DNA found in the plasma of cancer patients. Oncology, 1989. 46(5): p. 318-322
[79] Hollstein M, Sidransky D, Vogelstein B, Harris C C. p53 mutations in human cancers. Science (Wash D C) 1991; 253:49-53.
[80] Liu T, Wahlberg S, Burek E, Lindblom P, Rubio C, Lindblom A. Microsatellite instability as a predictor of a mutation in a DNA mismatch repair gene in familial colorectal cancer. Genes Chromosomes Cancer 2000; 27: 17-25.
[81] Groden J, Thliveris A, Samowitz W, et al. Identification and characterization of the familial adenomatous polyposis *coli* gene. Cell 1991; 66:589-600.
[82] Grunkemeler G L, Jin R. Receiver operating characteristic curve analysis of clinical risk models. Ann Thorac Surg 2001; 72:323-326.
[83]. Kharchenko S V, Shpakov A A. [Regulation of the RNase activity of the saliva in healthy subjects and in stomach cancer]. Izv Akad Nauk SSSR Biol 1989:58-63.
[84]. Myers L L, Wax M K. Positron emission tomography in the evaluation of the negative neck in patients with oral cavity cancer. J Otolaryngol 1998; 27:342-347.
[85] Mashberg A, Samit A. Early diagnosis of asymptomatic oral and oropharyngeal squamous cancers. C A Cancer J Clin 1995; 45:328-51.
[86] Rosin M P, Epstein J B, Berean K, et al. The use of exfoliative cell samples to map clonal genetic alterations in the oral epithelium of high-risk patients. Cancer Res 1997; 57:5258-5260.
[87] Streckfus C, Bigler L, Dellinger T, Dai X, Kingman A, Thigpen J T. The presence of soluble c-erbB-2 in saliva and serum among women with breast carcinoma: a preliminary study. Clin Cancer Res 2000; 6: 2363-2370.
[88] Unoki M, Nakamura Y. Growth-suppressive effects of BPO2 and EGR2, two genes involved in the PTEN signaling pathway. Oncogene 2001; 20:4457-4465.

[89] Suzuki C, Unoki M, Nakamura Y. Identification and allelic frequencies of novel single-nucleotide polymorphisms in the DUSP1 and BTG1 genes. J Hum Genet 2001; 46:155-157.

[90] Bettuzzi S, Davalli P, Astancolle S, et al. Tumor progression is accompanied by significant changes in the levels of expression of polyamine metabolism regulatory genes and clusterin (sulfated glycoprotein 2) in human prostate cancer specimens. Cancer Res 2000; 60: 28-34.

[91] Torelli G, Venturelli D, Colo A, et al. Expression of c-myb protooncogene and other cell cycle-related genes in normal and neoplastic human colonic mucosa. Cancer Res 1987; 47:5266-5269.

[92] Tsuji T, Usui S, Aida T, et al. Induction of epithelial differentiation and DNA demethylation in hamster malignant oral keratinocyte by ornithine decarboxylase antizyme. Oncogene 2001; 20:24-33.

[93] Gribenko A, Lopez M M, Richardson J M III, Makhatadze G I. Cloning, overexpression, purification, and spectroscopic characterization of human S100P. Protein Sci 1998; 7:211-215.

[94] Guerreiro Da Silva I D, Hu Y F, Russo I H, et al. S100P calciumbinding protein overexpression is associated with immortalization of human breast epithelial cells in vitro and early stages of breast cancer development in vivo. Int J Oncol 2000; 16:231-240.

[95] Mousses S, Bubendorf L, Wagner U, et al. Clinical validation of candidate genes associated with prostate cancer progression in the CWR22 model system using tissue microarrays. Cancer Res 2002; 62: 1256-1260.

[96] Mackay A, Jones C, Dexter I, et al. cDNA microarray analysis or genes associated with ERBB2 (HER2/neu) overexpression in human mammary luminal epithelial cells. Oncogene 2003; 22:2680-2688.

[97] Logsdon C D, Simeone D M, Binkley C, et al. Molecular profiling of pancreatic adenocarcinoma and chronic pancreatitis identifies multiple genes differentially regulated in pancreatic cancer. Cancer Res 2003; 63: 2649-2657.

[98] Cmogorac-Jurcevic T, Missiaglia E, Blayeri E, at al. Molecular alterations in pancreatic carcinoma: expression profiling shows that dysregulated expression of S100 genes is highly prevalent. J Pathol 2003; 201:63-74.

[99] Jablonska E, Piotrowski L, Grabowska Z. Serum Levels of IL-1b, IL6, TNF-a, sTNF-RI and CRP in patients with oral cavity cancer. Pathol Oncol Res 1997; 3:126-129.

[100] Chen C K, Wu M Y, Chao K H, Ho H N, Sheu B C, Huang S C. T lymphocytes and cytokine production in ascitic fluid of ovarian malignancies. J Formos Med Assoc 1999; 98:24-30.

[101] Hamajima N, Yuasa H. [Genetic polymorphisms related to interleukin-1 beta production and disease risk]. Nippon Koshu Eisei Zasshi 2003; 50:194-207.

[102] El-Omar E M, Rabkin C S, Gammon M D, et al. Increased risk of noncardia gastric cancer associated with proinflammatory cytokine gene polymorphisms. Gastroenterology 2003; 124:1193-1201.

[103] Malamud D. Oral diagnostic testing for detecting human immunodeficiency virus-1 antibodies: a technology whose time has come. Am J Med 1997; 102:9-14.

[104] Guven Y, Satman I, Dinccag N, Alptekin S. Salivary peroxidase activity in whole saliva of patients with insulin-dependent (type-1) diabetes mellitus. J Clin Periodontol 1996; 23:879-881.

[105] Lee J J, Hong W K, Hillerman W N, et al. Predicting cancer development in oral leukoplakia: ten years of translational research. Clin Cancer Res 2000; 6:1702-1710.

[106] Silverman S Jr, Gorsky M. Proliferative verrucous leukoplakia: a follow-up study of 54 cases. Oral Surg Oral Med Oral Pathol Oral Radiol Endod 1997; 84:154-157.

[107] Sudbo J, Kildal W, Risberg B, Koppang H S, Danielsen H E, Reith A. DNA content as a prognostic marker in patients with oral leukoplakia. N Engl J Med 2001; 344:1270-1278.

[108] Berta G N, Ghezzo F, D'Avolio A, et al. Enhancement of calcyclin gene RNA expression in squamous cell carcinoma of the oral mucosa, but not in benign lesions. J Oral Pathol Med 1997; 26:206-210.

[109] Watanabe H, Iwase M, Ohashi M, Nagumo M. Role of interleukin-8 secreted from human oral squamous cell carcinoma cell lines. Oral Oncol 2002; 38:670-679.

What is claimed is:

1. A method of detecting IL8 protein in a saliva sample of a subject comprising the steps of:

measuring the amount of IL8 protein in a saliva sample of a subject;

detecting that the amount of IL8 protein in the saliva sample of the subject is elevated relative to the amount of IL8 protein in saliva of a control subject known to not have a cancer of the oral cavity;

detecting that the subject has a cancer of the oral cavity when the amount of IL8 protein in the saliva sample of the subject is elevated relative to amount of IL8 protein in saliva of the control subject known to not have a cancer of the oral cavity; and administering a treatment of the cancer of the oral cavity to the subject, wherein the treatment is at least one selected from the group consisting of chemotherapy, radiation, and surgery.

2. The method of claim 1, wherein the cancer of the oral cavity is a cancer of the oropharynx.

3. The method of claim 1, wherein the cancer of the oral cavity is oropharyngeal squamous cell carcinoma.

4. The method of claim 1, wherein the cancer of the oral cavity is head and neck squamous cell carcinoma.

5. The method of claim 1, wherein the method comprises contacting the saliva sample with a reagent that specifically binds to IL8 protein.

6. The method of claim 5, wherein the reagent is an antibody.

* * * * *

SEQUENCE LISTING

```
<160> NUMBER OF SEQ ID NOS: 53

<210> SEQ ID NO 1
<211> LENGTH: 22
<212> TYPE: DNA
<213> ORGANISM: Artificial Sequence
<220> FEATURE:
<223> OTHER INFORMATION: house-keeping gene glyceraldehyde-3-phosphate
      dehydrogenase (GADPH) RT-PCR synthetic primer

<400> SEQUENCE: 1
tcaccagggc tgcttttaac tc                                                  22

<210> SEQ ID NO 2
<211> LENGTH: 22
<212> TYPE: DNA
<213> ORGANISM: Artificial Sequence
<220> FEATURE:
<223> OTHER INFORMATION: house-keeping gene glyceraldehyde-3-phosphate
      dehydrogenase (GADPH) RT-PCR synthetic primer

<400> SEQUENCE: 2
atgacaagct tcccgttctc ag                                                  22
```

<210> SEQ ID NO 3
<211> LENGTH: 22
<212> TYPE: DNA
<213> ORGANISM: Artificial Sequence
<220> FEATURE:
<223> OTHER INFORMATION: house-keeping gene beta-actin (actin-beta,
      ACTB) RT-PCR synthetic primer

<400> SEQUENCE: 3
aggatgcaga aggagatcac tg                                        22

<210> SEQ ID NO 4
<211> LENGTH: 22
<212> TYPE: DNA
<213> ORGANISM: Artificial Sequence
<220> FEATURE:
<223> OTHER INFORMATION: house-keeping gene beta-actin (actin-beta,
      ACTB) RT-PCR synthetic primer

<400> SEQUENCE: 4
atactcctgc ttgctgatcc ac                                        22

<210> SEQ ID NO 5
<211> LENGTH: 23
<212> TYPE: DNA
<213> ORGANISM: Artificial Sequence
<220> FEATURE:
<223> OTHER INFORMATION: house-keeping gene ribosomal protein S9 (RPS9)
      RT-PCR synthetic primer

<400> SEQUENCE: 5
gacccttcga gaaatctcgt ctc                                       23

<210> SEQ ID NO 6
<211> LENGTH: 22
<212> TYPE: DNA
<213> ORGANISM: Artificial Sequence
<220> FEATURE:
<223> OTHER INFORMATION: house-keeping gene ribosomal protein S9 (RPS9)
      RT-PCR synthetic primer

<400> SEQUENCE: 6
tctcatcaag cgtcagcagt tc                                        22

<210> SEQ ID NO 7
<211> LENGTH: 22
<212> TYPE: DNA
<213> ORGANISM: Artificial Sequence
<220> FEATURE:
<223> OTHER INFORMATION: interleukin 1, beta (IL1B) Q-PCR synthetic
      primer

<400> SEQUENCE: 7
gtgctgaatg tggactcaat cc                                        22

<210> SEQ ID NO 8
<211> LENGTH: 19
<212> TYPE: DNA
<213> ORGANISM: Artificial Sequence
<220> FEATURE:
<223> OTHER INFORMATION: interleukin 1, beta (IL1B) Q-PCR synthetic
      primer

<400> SEQUENCE: 8
accctaaggc aggcagttg                                            19

```
<210> SEQ ID NO 9
<211> LENGTH: 20
<212> TYPE: DNA
<213> ORGANISM: Artificial Sequence
<220> FEATURE:
<223> OTHER INFORMATION: stratifin (SFN) Q-PCR synthetic primer

<400> SEQUENCE: 9
cctgcgaaga gcgaaacctg                                               20

<210> SEQ ID NO 10
<211> LENGTH: 22
<212> TYPE: DNA
<213> ORGANISM: Artificial Sequence
<220> FEATURE:
<223> OTHER INFORMATION: stratifin (SFN) Q-PCR synthetic primer

<400> SEQUENCE: 10
tcaatactgg acagcaccct cc                                            22

<210> SEQ ID NO 11
<211> LENGTH: 19
<212> TYPE: DNA
<213> ORGANISM: Artificial Sequence
<220> FEATURE:
<223> OTHER INFORMATION: tubulin, alpha, ubiquitous (K-ALPHA-1) Q-PCR
      synthetic primer

<400> SEQUENCE: 11
agcgtgcctt tgttcactg                                                19

<210> SEQ ID NO 12
<211> LENGTH: 22
<212> TYPE: DNA
<213> ORGANISM: Artificial Sequence
<220> FEATURE:
<223> OTHER INFORMATION: tubulin, alpha, ubiquitous (K-ALPHA-1) Q-PCR
      synthetic primer

<400> SEQUENCE: 12
cacaccaacc tcctcataat cc                                            22

<210> SEQ ID NO 13
<211> LENGTH: 22
<212> TYPE: DNA
<213> ORGANISM: Artificial Sequence
<220> FEATURE:
<223> OTHER INFORMATION: beta-actin (ACTB) RT-PCR and qRT-PCR synthetic
      oligonucleotide primer

<400> SEQUENCE: 13
aggatgcaga aggagatcac tg                                            22

<210> SEQ ID NO 14
<211> LENGTH: 22
<212> TYPE: DNA
<213> ORGANISM: Artificial Sequence
<220> FEATURE:
<223> OTHER INFORMATION: beta-actin (ACTB)  RT-PCR and qRT-PCR synthetic
      oligonucleotide primer

<400> SEQUENCE: 14
atactcctgc ttgctgatcc ac                                            22

<210> SEQ ID NO 15
<211> LENGTH: 22
```

```
<212> TYPE: DNA
<213> ORGANISM: Artificial Sequence
<220> FEATURE:
<223> OTHER INFORMATION: interleukin 8 (IL8) RT-PCR and qRT-PCR
      synthetic oligonucleotide primer

<400> SEQUENCE: 15
gagggttgtg gagaagtttt tg                                           22

<210> SEQ ID NO 16
<211> LENGTH: 22
<212> TYPE: DNA
<213> ORGANISM: Artificial Sequence
<220> FEATURE:
<223> OTHER INFORMATION: interleukin 8 (IL8) RT-PCR and qRT-PCR
      synthetic oligonucleotide primer

<400> SEQUENCE: 16
ctggcatctt cactgattct tg                                           22

<210> SEQ ID NO 17
<211> LENGTH: 21
<212> TYPE: DNA
<213> ORGANISM: Artificial Sequence
<220> FEATURE:
<223> OTHER INFORMATION: interleukin 6 (IL6) RT-PCR and qRT-PCR
      synthetic oligonucleotide primer

<400> SEQUENCE: 17
ctggcagaaa acaacctgaa c                                            21

<210> SEQ ID NO 18
<211> LENGTH: 21
<212> TYPE: DNA
<213> ORGANISM: Artificial Sequence
<220> FEATURE:
<223> OTHER INFORMATION: interleukin 6 (IL6) RT-PCR and qRT-PCR
      synthetic oligonucleotide primer

<400> SEQUENCE: 18
atgattttca ccaggcaagt c                                            21

<210> SEQ ID NO 19
<211> LENGTH: 18
<212> TYPE: DNA
<213> ORGANISM: Artificial Sequence
<220> FEATURE:
<223> OTHER INFORMATION: housekeeping gene beta-actin (ACTB) RT-PCR
      synthetic oligonucleotide upstream primer F

<400> SEQUENCE: 19
cgtcttcccc tccatcgt                                                18

<210> SEQ ID NO 20
<211> LENGTH: 23
<212> TYPE: DNA
<213> ORGANISM: Artificial Sequence
<220> FEATURE:
<223> OTHER INFORMATION: housekeeping gene beta-actin (ACTB) RT-PCR
      synthetic oligonucleotide downstream primer R1

<400> SEQUENCE: 20
agctcattgt agaaggtgtg gtg                                          23

<210> SEQ ID NO 21
<211> LENGTH: 22
<212> TYPE: DNA
```

```
<213> ORGANISM: Artificial Sequence
<220> FEATURE:
<223> OTHER INFORMATION: housekeeping gene beta-actin (ACTB) RT-PCR
      synthetic oligonucleotide downstream primer R2

<400> SEQUENCE: 21
atactcctgc ttgctgatcc ac                                              22

<210> SEQ ID NO 22
<211> LENGTH: 23
<212> TYPE: DNA
<213> ORGANISM: Artificial Sequence
<220> FEATURE:
<223> OTHER INFORMATION: housekeeping gene beta-actin (ACTB) RT-PCR
      synthetic oligonucleotide downstream primer R3

<400> SEQUENCE: 22
ggtgtgcact tttattcaac tgg                                             23

<210> SEQ ID NO 23
<211> LENGTH: 20
<212> TYPE: DNA
<213> ORGANISM: Artificial Sequence
<220> FEATURE:
<223> OTHER INFORMATION: housekeeping gene beta-2-microglobulin (B2M)
      RT-PCR synthetic oligonucleotide upstream primer F

<400> SEQUENCE: 23
gtgctcgcgc tactctctct                                                 20

<210> SEQ ID NO 24
<211> LENGTH: 20
<212> TYPE: DNA
<213> ORGANISM: Artificial Sequence
<220> FEATURE:
<223> OTHER INFORMATION: housekeeping gene beta-2-microglobulin (B2M)
      RT-PCR synthetic oligonucleotide downstream primer R1

<400> SEQUENCE: 24
ccagtccttg ctgaaagaca                                                 20

<210> SEQ ID NO 25
<211> LENGTH: 20
<212> TYPE: DNA
<213> ORGANISM: Artificial Sequence
<220> FEATURE:
<223> OTHER INFORMATION: housekeeping gene beta-2-microglobulin (B2M)
      RT-PCR synthetic oligonucleotide downstream primer R2

<400> SEQUENCE: 25
ttctctgctc cccacctcta                                                 20

<210> SEQ ID NO 26
<211> LENGTH: 21
<212> TYPE: DNA
<213> ORGANISM: Artificial Sequence
<220> FEATURE:
<223> OTHER INFORMATION: housekeeping gene beta-2-microglobulin (B2M)
      RT-PCR synthetic oligonucleotide downstream primer R3

<400> SEQUENCE: 26
ccagattaac cacaaccatg c                                               21

<210> SEQ ID NO 27
<211> LENGTH: 22
<212> TYPE: DNA
<213> ORGANISM: Artificial Sequence
```

```
<220> FEATURE:
<223> OTHER INFORMATION: housekeeping gene glyceraldehyde-3-phosphate
      dehydrogenase (GADPH) RT-PCR synthetic oligonucleotide upstream
      primer F

<400> SEQUENCE: 27
gagtcaacgg atttggtcgt at                                            22

<210> SEQ ID NO 28
<211> LENGTH: 22
<212> TYPE: DNA
<213> ORGANISM: Artificial Sequence
<220> FEATURE:
<223> OTHER INFORMATION: housekeeping gene glyceraldehyde-3-phosphate
      dehydrogenase (GADPH) RT-PCR synthetic oligonucleotide downstream
      primer R1

<400> SEQUENCE: 28
atgggtggaa tcatattgga ac                                            22

<210> SEQ ID NO 29
<211> LENGTH: 23
<212> TYPE: DNA
<213> ORGANISM: Artificial Sequence
<220> FEATURE:
<223> OTHER INFORMATION: housekeeping gene glyceraldehyde-3-phosphate
      dehydrogenase (GADPH) RT-PCR synthetic oligonucleotide downstream
      primer R2

<400> SEQUENCE: 29
gatgtcatca tatttggcag gtt                                           23

<210> SEQ ID NO 30
<211> LENGTH: 23
<212> TYPE: DNA
<213> ORGANISM: Artificial Sequence
<220> FEATURE:
<223> OTHER INFORMATION: housekeeping gene glyceraldehyde-3-phosphate
      dehydrogenase (GADPH) RT-PCR synthetic oligonucleotide downstream
      primer R3

<400> SEQUENCE: 30
agcacagggt actttattga tgg                                           23

<210> SEQ ID NO 31
<211> LENGTH: 20
<212> TYPE: DNA
<213> ORGANISM: Artificial Sequence
<220> FEATURE:
<223> OTHER INFORMATION: housekeeping gene ribosomal protein S9 (RPS9)
      RT-PCR synthetic oligonucleotide upstream primer F

<400> SEQUENCE: 31
ctgggtttgt cgcaaaactt                                               20

<210> SEQ ID NO 32
<211> LENGTH: 20
<212> TYPE: DNA
<213> ORGANISM: Artificial Sequence
<220> FEATURE:
<223> OTHER INFORMATION: housekeeping gene ribosomal protein S9 (RPS9)
      RT-PCR synthetic oligonucleotide downstream primer R1

<400> SEQUENCE: 32
gtgggtcctt ctcatcaagc                                               20

<210> SEQ ID NO 33
```

-continued

<211> LENGTH: 20
<212> TYPE: DNA
<213> ORGANISM: Artificial Sequence
<220> FEATURE:
<223> OTHER INFORMATION: housekeeping gene ribosomal protein S9 (RPS9)
      RT-PCR synthetic oligonucleotide downstream primer R2

<400> SEQUENCE: 33
atgaaggacg ggatgttcac                                                    20

<210> SEQ ID NO 34
<211> LENGTH: 20
<212> TYPE: DNA
<213> ORGANISM: Artificial Sequence
<220> FEATURE:
<223> OTHER INFORMATION: housekeeping gene ribosomal protein S9 (RPS9)
      RT-PCR synthetic oligonucleotide downstream primer R3

<400> SEQUENCE: 34
ggcaggaaaa cgagacaatc                                                    20

<210> SEQ ID NO 35
<211> LENGTH: 22
<212> TYPE: DNA
<213> ORGANISM: Artificial Sequence
<220> FEATURE:
<223> OTHER INFORMATION: dual specificity phosphatase 1 (DUSP1) Q-PCR
      primer F

<400> SEQUENCE: 35
cctaccagta ttattcccga cg                                                 22

<210> SEQ ID NO 36
<211> LENGTH: 22
<212> TYPE: DNA
<213> ORGANISM: Artificial Sequence
<220> FEATURE:
<223> OTHER INFORMATION: dual specificity phosphatase 1 (DUSP1) Q-PCR
      primer R

<400> SEQUENCE: 36
ttgtgaaggc agacacctac ac                                                 22

<210> SEQ ID NO 37
<211> LENGTH: 19
<212> TYPE: DNA
<213> ORGANISM: Artificial Sequence
<220> FEATURE:
<223> OTHER INFORMATION: H3 histone, family 3A (H3F3A) Q-PCR primer F

<400> SEQUENCE: 37
aaagcaccca ggaagcaac                                                     19

<210> SEQ ID NO 38
<211> LENGTH: 22
<212> TYPE: DNA
<213> ORGANISM: Artificial Sequence
<220> FEATURE:
<223> OTHER INFORMATION: H3 histone, family 3A (H3F3A) Q-PCR primer R

<400> SEQUENCE: 38
gcgaatcaga agttcagtgg ac                                                 22

<210> SEQ ID NO 39
<211> LENGTH: 22
<212> TYPE: DNA
<213> ORGANISM: Artificial Sequence

```
<220> FEATURE:
<223> OTHER INFORMATION: interleukin 1beta (IL1B) Q-PCR primer F

<400> SEQUENCE: 39
gtgctgaatg tggactcaat cc                                              22

<210> SEQ ID NO 40
<211> LENGTH: 19
<212> TYPE: DNA
<213> ORGANISM: Artificial Sequence
<220> FEATURE:
<223> OTHER INFORMATION: interleukin 1beta (IL1B) Q-PCR primer R

<400> SEQUENCE: 40
accctaaggc aggcagttg                                                  19

<210> SEQ ID NO 41
<211> LENGTH: 22
<212> TYPE: DNA
<213> ORGANISM: Artificial Sequence
<220> FEATURE:
<223> OTHER INFORMATION: interleukin 8 (IL8) Q-PCR primer F

<400> SEQUENCE: 41
gagggttgtg gagaagtttt tg                                              22

<210> SEQ ID NO 42
<211> LENGTH: 22
<212> TYPE: DNA
<213> ORGANISM: Artificial Sequence
<220> FEATURE:
<223> OTHER INFORMATION: interleukin 8 (IL8) Q-PCR primer R

<400> SEQUENCE: 42
ctggcatctt cactgattct tg                                              22

<210> SEQ ID NO 43
<211> LENGTH: 21
<212> TYPE: DNA
<213> ORGANISM: Artificial Sequence
<220> FEATURE:
<223> OTHER INFORMATION: ornithine decarboxylase antizyme 1 (OAZ1)
      Q-PCR primer F

<400> SEQUENCE: 43
agagagagtc ttcgggagag g                                               21

<210> SEQ ID NO 44
<211> LENGTH: 21
<212> TYPE: DNA
<213> ORGANISM: Artificial Sequence
<220> FEATURE:
<223> OTHER INFORMATION: ornithine decarboxylase antizyme 1 (OAZ1)
      Q-PCR primer R

<400> SEQUENCE: 44
agatgagcga gtctacggtt c                                               21

<210> SEQ ID NO 45
<211> LENGTH: 22
<212> TYPE: DNA
<213> ORGANISM: Artificial Sequence
<220> FEATURE:
<223> OTHER INFORMATION: S100 calcium binding protein P (S100P)
      Q-PCR primer F

<400> SEQUENCE: 45
```

```
gagttcatcg tgttcgtggc tg                                              22
```

<210> SEQ ID NO 46
<211> LENGTH: 22
<212> TYPE: DNA
<213> ORGANISM: Artificial Sequence
<220> FEATURE:
<223> OTHER INFORMATION: S100 calcium binding protein P (S100P)
     Q-PCR primer R

<400> SEQUENCE: 46

```
ctccagggca tcatttgagt cc                                              22
```

<210> SEQ ID NO 47
<211> LENGTH: 21
<212> TYPE: DNA
<213> ORGANISM: Artificial Sequence
<220> FEATURE:
<223> OTHER INFORMATION: spermidine/spermine N1-acetyltransferase (SAT)
     Q-PCR primer F

<400> SEQUENCE: 47

```
ccagtgaaga gggttggaga c                                               21
```

<210> SEQ ID NO 48
<211> LENGTH: 22
<212> TYPE: DNA
<213> ORGANISM: Artificial Sequence
<220> FEATURE:
<223> OTHER INFORMATION: spermidine/spermine N1-acetyltransferase (SAT)
     Q-PCR primer R

<400> SEQUENCE: 48

```
tggaggttgt catctacagc ag                                              22
```

<210> SEQ ID NO 49
<211> LENGTH: 20
<212> TYPE: DNA
<213> ORGANISM: Artificial Sequence
<220> FEATURE:
<223> OTHER INFORMATION: growth arrest and DNA-damage-inducible beta
     (GADD45B) Q-PCR primer F

<400> SEQUENCE: 49

```
tgatgaatgt ggacccagac                                                 20
```

<210> SEQ ID NO 50
<211> LENGTH: 19
<212> TYPE: DNA
<213> ORGANISM: Artificial Sequence
<220> FEATURE:
<223> OTHER INFORMATION: growth arrest and DNA-damage-inducible beta
     (GADD45B) Q-PCR primer R

<400> SEQUENCE: 50

```
gagcgtgaag tggatttgc                                                  19
```

<210> SEQ ID NO 51
<211> LENGTH: 22
<212> TYPE: DNA
<213> ORGANISM: Artificial Sequence
<220> FEATURE:
<223> OTHER INFORMATION: regulator of G-protein signaling 2, 24 kda
     (RGS2) Q-PCR primer F

<400> SEQUENCE: 51

```
cctgccataa agactgacct tg                                              22

<210> SEQ ID NO 52
<211> LENGTH: 22
<212> TYPE: DNA
<213> ORGANISM: Artificial Sequence
<220> FEATURE:
<223> OTHER INFORMATION: regulator of G-protein signaling 2, 24 kda
      (RGS2) Q-PCR primer R

<400> SEQUENCE: 52
gcttcctgat tcactaccca ac                                              22

<210> SEQ ID NO 53
<211> LENGTH: 24
<212> TYPE: DNA
<213> ORGANISM: Artificial Sequence
<220> FEATURE:
<223> OTHER INFORMATION: T7-oligo-(dT)-24 RT primer for amplification
      of first strand cDNA

<400> SEQUENCE: 53
tttttttttt tttttttttt tttt                                            24
```